United States Patent
Lang et al.

(10) Patent No.: US 9,053,527 B2
(45) Date of Patent: *Jun. 9, 2015

(54) DETECTING DEFECTS ON A WAFER

(71) Applicant: KLA-Tencor Corporation, Milpitas, CA (US)

(72) Inventors: Jun Lang, Union City, CA (US); Kan Chen, Fremont, CA (US); Lisheng Gao, Morgan Hill, CA (US); Junqing Huang, Fremont, CA (US)

(73) Assignee: KLA-Tencor Corp., Milpitas, CA (US)

( * ) Notice: Subject to any disclaimer, the term of this patent is extended or adjusted under 35 U.S.C. 154(b) by 216 days.

This patent is subject to a terminal disclaimer.

(21) Appl. No.: 13/733,133

(22) Filed: Jan. 2, 2013

(65) Prior Publication Data

US 2014/0185919 A1 Jul. 3, 2014

(51) Int. Cl.
- G06K 9/00 (2006.01)
- G06T 7/00 (2006.01)
- G03F 7/20 (2006.01)

(Continued)

(52) U.S. Cl.
CPC ............. *G06T 7/0004* (2013.01); *G06T 7/0008* (2013.01); *G03F 7/70616* (2013.01); *G06T 2207/10152* (2013.01); *G06T 2207/30148* (2013.01); *G01N 21/8851* (2013.01); *G01N 21/9501* (2013.01); *G01N 2021/8867* (2013.01)

(58) Field of Classification Search
CPC ................ G06T 7/0004; G06T 7/0008; G06T 2207/30148
USPC .................................................. 382/145, 149
See application file for complete search history.

(56) References Cited

U.S. PATENT DOCUMENTS

| 3,495,269 A | 2/1970 | Mutschler et al. |
| 3,496,352 A | 2/1970 | Jugle |
| 3,909,602 A | 9/1975 | Micka |

(Continued)

FOREIGN PATENT DOCUMENTS

| CN | 1339140 | 3/2002 |
| CN | 1398348 | 2/2003 |

(Continued)

OTHER PUBLICATIONS

Guo et al., "License Plate Localization and Character Segmentation with Feedback Self-Learning and Hybrid Binarization Techniques," IEEE Transactions on Vehicular Technology, vol. 57, No. 3, May 2008, pp. 1417-1424.

(Continued)

*Primary Examiner* — Utpal Shah
(74) *Attorney, Agent, or Firm* — Ann Marie Mewherter

(57) ABSTRACT

Methods and systems for detecting defects on a wafer are provided. One method includes identifying one or more characteristics of first raw output generated for a wafer that correspond to one or more geometrical characteristics of patterned features formed on the wafer and assigning individual output in second raw output generated for the wafer to different segments based on the identified one or more characteristics of the first raw output and based on the individual output in the second raw output and individual output in the first raw output that were generated at substantially the same locations on the wafer such that the one or more geometrical characteristics of the patterned features that correspond to each of the different segments in the second raw output are different.

51 Claims, 3 Drawing Sheets

(51) Int. Cl.
*G01N 21/88* (2006.01)
*G01N 21/95* (2006.01)

(56) References Cited

U.S. PATENT DOCUMENTS

| | | | |
|---|---|---|---|
| 4,015,203 A | 3/1977 | Verkuil | |
| 4,247,203 A | 1/1981 | Levy et al. | |
| 4,347,001 A | 8/1982 | Levy et al. | |
| 4,378,159 A | 3/1983 | Galbraith | |
| 4,448,532 A | 5/1984 | Joseph et al. | |
| 4,475,122 A | 10/1984 | Green | |
| 4,532,650 A | 7/1985 | Wihl et al. | |
| 4,555,798 A | 11/1985 | Broadbent, Jr. et al. | |
| 4,578,810 A | 3/1986 | MacFarlane et al. | |
| 4,579,455 A | 4/1986 | Levy et al. | |
| 4,595,289 A | 6/1986 | Feldman et al. | |
| 4,599,558 A | 7/1986 | Castellano, Jr. et al. | |
| 4,633,504 A | 12/1986 | Wihl | |
| 4,641,353 A | 2/1987 | Kobayashi | |
| 4,641,967 A | 2/1987 | Pecen | |
| 4,734,721 A | 3/1988 | Boyer et al. | |
| 4,748,327 A | 5/1988 | Shinozaki et al. | |
| 4,758,094 A | 7/1988 | Wihl et al. | |
| 4,766,324 A | 8/1988 | Saadat et al. | |
| 4,799,175 A | 1/1989 | Sano et al. | |
| 4,805,123 A | 2/1989 | Specht et al. | |
| 4,812,756 A | 3/1989 | Curtis et al. | |
| 4,814,829 A | 3/1989 | Kosugi et al. | |
| 4,817,123 A | 3/1989 | Sones et al. | |
| 4,845,558 A | 7/1989 | Tsai et al. | |
| 4,877,326 A | 10/1989 | Chadwick et al. | |
| 4,926,489 A | 5/1990 | Danielson et al. | |
| 4,928,313 A | 5/1990 | Leonard et al. | |
| 5,046,109 A | 9/1991 | Fujimori et al. | |
| 5,124,927 A | 6/1992 | Hopewell et al. | |
| 5,189,481 A | 2/1993 | Jann et al. | |
| 5,355,212 A | 10/1994 | Wells et al. | |
| 5,444,480 A | 8/1995 | Sumita | |
| 5,453,844 A | 9/1995 | George et al. | |
| 5,481,624 A | 1/1996 | Kamon | |
| 5,485,091 A | 1/1996 | Verkuil | |
| 5,497,381 A | 3/1996 | O'Donoghue et al. | |
| 5,528,153 A | 6/1996 | Taylor et al. | |
| 5,544,256 A | 8/1996 | Brecher et al. | |
| 5,563,702 A | 10/1996 | Emery et al. | |
| 5,572,598 A | 11/1996 | Wihl et al. | |
| 5,578,821 A | 11/1996 | Meisberger et al. | |
| 5,594,247 A | 1/1997 | Verkuil et al. | |
| 5,608,538 A | 3/1997 | Edgar et al. | |
| 5,619,548 A | 4/1997 | Koppel | |
| 5,621,519 A | 4/1997 | Frost et al. | |
| 5,644,223 A | 7/1997 | Verkuil | |
| 5,650,731 A | 7/1997 | Fung et al. | |
| 5,661,408 A | 8/1997 | Kamieniecki et al. | |
| 5,689,614 A | 11/1997 | Gronet et al. | |
| 5,694,478 A | 12/1997 | Braier et al. | |
| 5,696,835 A | 12/1997 | Hennessey et al. | |
| 5,703,969 A | 12/1997 | Hennessey et al. | |
| 5,716,889 A | 2/1998 | Tsuji et al. | |
| 5,737,072 A | 4/1998 | Emery et al. | |
| 5,742,658 A | 4/1998 | Tiffin et al. | |
| 5,754,678 A | 5/1998 | Hawthorne et al. | |
| 5,767,691 A | 6/1998 | Verkuil | |
| 5,767,693 A | 6/1998 | Verkuil | |
| 5,771,317 A | 6/1998 | Edgar | |
| 5,773,989 A | 6/1998 | Edelman et al. | |
| 5,774,179 A | 6/1998 | Chevrette et al. | |
| 5,795,685 A | 8/1998 | Liebmann et al. | |
| 5,822,218 A | 10/1998 | Moosa et al. | |
| 5,831,865 A | 11/1998 | Berezin et al. | |
| 5,834,941 A | 11/1998 | Verkuil | |
| 5,852,232 A | 12/1998 | Samsavar et al. | |
| 5,866,806 A | 2/1999 | Samsavar et al. | |
| 5,874,733 A | 2/1999 | Silver et al. | |
| 5,884,242 A | 3/1999 | Meier et al. | |
| 5,889,593 A | 3/1999 | Bareket | |
| 5,917,332 A | 6/1999 | Chen et al. | |
| 5,932,377 A | 8/1999 | Ferguson et al. | |
| 5,940,458 A | 8/1999 | Suk | |
| 5,948,972 A | 9/1999 | Samsavar et al. | |
| 5,955,661 A | 9/1999 | Samsavar et al. | |
| 5,965,306 A | 10/1999 | Mansfield et al. | |
| 5,978,501 A | 11/1999 | Badger et al. | |
| 5,980,187 A | 11/1999 | Verhovsky | |
| 5,986,263 A | 11/1999 | Hiroi et al. | |
| 5,991,699 A | 11/1999 | Kulkarni et al. | |
| 5,999,003 A | 12/1999 | Steffan et al. | |
| 6,011,404 A | 1/2000 | Ma et al. | |
| 6,014,461 A | 1/2000 | Hennessey et al. | |
| 6,040,911 A | 3/2000 | Nozaki et al. | |
| 6,040,912 A | 3/2000 | Zika et al. | |
| 6,052,478 A | 4/2000 | Wihl et al. | |
| 6,060,709 A | 5/2000 | Verkuil et al. | |
| 6,072,320 A | 6/2000 | Verkuil | |
| 6,076,465 A | 6/2000 | Vacca et al. | |
| 6,078,738 A | 6/2000 | Garza et al. | |
| 6,091,257 A | 7/2000 | Verkuil et al. | |
| 6,091,846 A | 7/2000 | Lin et al. | |
| 6,097,196 A | 8/2000 | Verkuil et al. | |
| 6,097,887 A | 8/2000 | Hardikar et al. | |
| 6,104,206 A | 8/2000 | Verkuil | |
| 6,104,835 A | 8/2000 | Han | |
| 6,117,598 A | 9/2000 | Imai | |
| 6,121,783 A | 9/2000 | Horner et al. | |
| 6,122,017 A | 9/2000 | Taubman | |
| 6,122,046 A | 9/2000 | Almogy | |
| 6,137,570 A | 10/2000 | Chuang et al. | |
| 6,141,038 A | 10/2000 | Young et al. | |
| 6,146,627 A | 11/2000 | Muller et al. | |
| 6,171,737 B1 | 1/2001 | Phan et al. | |
| 6,175,645 B1 | 1/2001 | Elyasaf et al. | |
| 6,184,929 B1 | 2/2001 | Noda et al. | |
| 6,184,976 B1 | 2/2001 | Park et al. | |
| 6,191,605 B1 | 2/2001 | Miller et al. | |
| 6,201,999 B1 | 3/2001 | Jevtic | |
| 6,202,029 B1 | 3/2001 | Verkuil et al. | |
| 6,205,239 B1 | 3/2001 | Lin et al. | |
| 6,215,551 B1 | 4/2001 | Nikoonahad et al. | |
| 6,224,638 B1 | 5/2001 | Jevtic et al. | |
| 6,233,719 B1 | 5/2001 | Hardikar et al. | |
| 6,246,787 B1 | 6/2001 | Hennessey et al. | |
| 6,248,485 B1 | 6/2001 | Cuthbert | |
| 6,248,486 B1 | 6/2001 | Dirksen et al. | |
| 6,259,960 B1 | 7/2001 | Inokuchi | |
| 6,266,437 B1 | 7/2001 | Eichel et al. | |
| 6,267,005 B1 | 7/2001 | Samsavar et al. | |
| 6,268,093 B1 | 7/2001 | Kenan et al. | |
| 6,272,236 B1 | 8/2001 | Pierrat et al. | |
| 6,282,309 B1 | 8/2001 | Emery | |
| 6,292,582 B1 | 9/2001 | Lin et al. | |
| 6,295,374 B1 | 9/2001 | Robinson et al. | |
| 6,324,298 B1 | 11/2001 | O'Dell et al. | |
| 6,344,640 B1 | 2/2002 | Rhoads | |
| 6,363,166 B1 | 3/2002 | Wihl et al. | |
| 6,366,687 B1 | 4/2002 | Aloni et al. | |
| 6,373,975 B1 | 4/2002 | Bula et al. | |
| 6,388,747 B2 | 5/2002 | Nara et al. | |
| 6,393,602 B1 | 5/2002 | Atchison et al. | |
| 6,407,373 B1 | 6/2002 | Dotan | |
| 6,415,421 B2 | 7/2002 | Anderson et al. | |
| 6,445,199 B1 | 9/2002 | Satya et al. | |
| 6,451,690 B1 | 9/2002 | Matsumoto et al. | |
| 6,459,520 B1 | 10/2002 | Takayama | |
| 6,466,314 B1 | 10/2002 | Lehman | |
| 6,466,315 B1 | 10/2002 | Karpol et al. | |
| 6,470,489 B1 | 10/2002 | Chang et al. | |
| 6,483,938 B1 | 11/2002 | Hennessey et al. | |
| 6,513,151 B1 | 1/2003 | Erhardt et al. | |
| 6,526,164 B1 | 2/2003 | Mansfield et al. | |
| 6,529,621 B1 | 3/2003 | Glasser et al. | |
| 6,535,628 B2 | 3/2003 | Smargiassi et al. | |
| 6,539,106 B1 | 3/2003 | Gallarda et al. | |
| 6,569,691 B1 | 5/2003 | Jastrzebski et al. | |
| 6,581,193 B1 | 6/2003 | McGhee et al. | |

(56) References Cited

U.S. PATENT DOCUMENTS

| | | |
|---|---|---|
| 6,593,748 B1 | 7/2003 | Halliyal et al. |
| 6,597,193 B2 | 7/2003 | Lagowski et al. |
| 6,602,728 B1 | 8/2003 | Liebmann et al. |
| 6,608,681 B2 | 8/2003 | Tanaka et al. |
| 6,614,520 B1 | 9/2003 | Bareket et al. |
| 6,631,511 B2 | 10/2003 | Haffner et al. |
| 6,636,301 B1 | 10/2003 | Kvamme et al. |
| 6,642,066 B1 | 11/2003 | Halliyal et al. |
| 6,658,640 B2 | 12/2003 | Weed |
| 6,665,065 B1 | 12/2003 | Phan et al. |
| 6,670,082 B2 | 12/2003 | Liu et al. |
| 6,680,621 B2 | 1/2004 | Savtchouk et al. |
| 6,691,052 B1 | 2/2004 | Maurer |
| 6,701,004 B1 | 3/2004 | Shykind et al. |
| 6,718,526 B1 | 4/2004 | Eldredge et al. |
| 6,721,695 B1 | 4/2004 | Chen et al. |
| 6,734,696 B2 | 5/2004 | Horner et al. |
| 6,738,954 B1 | 5/2004 | Allen et al. |
| 6,748,103 B2 | 6/2004 | Glasser et al. |
| 6,751,519 B1 | 6/2004 | Satya et al. |
| 6,753,954 B2 | 6/2004 | Chen |
| 6,757,645 B2 | 6/2004 | Chang et al. |
| 6,759,655 B2 | 7/2004 | Nara et al. |
| 6,771,806 B1 | 8/2004 | Satya et al. |
| 6,775,818 B2 | 8/2004 | Taravade et al. |
| 6,777,147 B1 | 8/2004 | Fonseca et al. |
| 6,777,676 B1 | 8/2004 | Wang et al. |
| 6,778,695 B1 | 8/2004 | Schellenberg et al. |
| 6,779,159 B2 | 8/2004 | Yokoyama et al. |
| 6,784,446 B1 | 8/2004 | Phan et al. |
| 6,788,400 B2 | 9/2004 | Chen |
| 6,789,032 B2 | 9/2004 | Barbour et al. |
| 6,803,554 B2 | 10/2004 | Ye et al. |
| 6,806,456 B1 | 10/2004 | Ye et al. |
| 6,807,503 B2 | 10/2004 | Ye et al. |
| 6,813,572 B2 | 11/2004 | Satya et al. |
| 6,820,028 B2 | 11/2004 | Ye et al. |
| 6,828,542 B2 | 12/2004 | Ye et al. |
| 6,842,225 B1 | 1/2005 | Irie |
| 6,859,746 B1 | 2/2005 | Stirton |
| 6,879,403 B2 | 4/2005 | Freifeld |
| 6,879,924 B2 | 4/2005 | Ye et al. |
| 6,882,745 B2 | 4/2005 | Brankner et al. |
| 6,884,984 B2 | 4/2005 | Ye et al. |
| 6,886,153 B1 | 4/2005 | Bevis |
| 6,892,156 B2 | 5/2005 | Ye et al. |
| 6,902,855 B2 | 6/2005 | Peterson et al. |
| 6,906,305 B2 | 6/2005 | Pease et al. |
| 6,918,101 B1 | 7/2005 | Satya et al. |
| 6,919,957 B2 | 7/2005 | Nikoonahad et al. |
| 6,937,753 B1 | 8/2005 | O'Dell et al. |
| 6,948,141 B2 | 9/2005 | Satya et al. |
| 6,959,255 B2 | 10/2005 | Ye et al. |
| 6,966,047 B1 | 11/2005 | Glasser |
| 6,969,837 B2 | 11/2005 | Ye et al. |
| 6,969,864 B2 | 11/2005 | Ye et al. |
| 6,983,060 B1 | 1/2006 | Martinent-Catalot et al. |
| 6,988,045 B2 | 1/2006 | Purdy |
| 6,990,385 B1 | 1/2006 | Smith et al. |
| 7,003,755 B2 | 2/2006 | Pang et al. |
| 7,003,758 B2 | 2/2006 | Ye et al. |
| 7,012,438 B1 | 3/2006 | Miller et al. |
| 7,026,615 B2 | 4/2006 | Takane et al. |
| 7,027,143 B1 | 4/2006 | Stokowski et al. |
| 7,030,966 B2 | 4/2006 | Hansen |
| 7,030,997 B2 | 4/2006 | Neureuther et al. |
| 7,053,355 B2 | 5/2006 | Ye et al. |
| 7,061,625 B1 | 6/2006 | Hwang et al. |
| 7,071,833 B2 | 7/2006 | Nagano et al. |
| 7,103,484 B1 | 9/2006 | Shi et al. |
| 7,106,895 B1 | 9/2006 | Goldberg et al. |
| 7,107,517 B1 | 9/2006 | Suzuki et al. |
| 7,107,571 B2 | 9/2006 | Chang et al. |
| 7,111,277 B2 | 9/2006 | Ye et al. |
| 7,114,143 B2 | 9/2006 | Hanson et al. |
| 7,114,145 B2 | 9/2006 | Ye et al. |
| 7,117,477 B2 | 10/2006 | Ye et al. |
| 7,117,478 B2 | 10/2006 | Ye et al. |
| 7,120,285 B1 | 10/2006 | Spence |
| 7,120,895 B2 | 10/2006 | Ye et al. |
| 7,123,356 B1 | 10/2006 | Stokowski et al. |
| 7,124,386 B2 | 10/2006 | Smith et al. |
| 7,133,548 B2 | 11/2006 | Kenan et al. |
| 7,135,344 B2 | 11/2006 | Nehmadi et al. |
| 7,136,143 B2 | 11/2006 | Smith |
| 7,152,215 B2 | 12/2006 | Smith et al. |
| 7,162,071 B2 | 1/2007 | Hung et al. |
| 7,170,593 B2 | 1/2007 | Honda et al. |
| 7,171,334 B2 | 1/2007 | Gassner |
| 7,174,520 B2 | 2/2007 | White et al. |
| 7,194,709 B2 | 3/2007 | Brankner |
| 7,207,017 B1 | 4/2007 | Tabery et al. |
| 7,231,628 B2 | 6/2007 | Pack et al. |
| 7,236,847 B2 | 6/2007 | Marella |
| 7,271,891 B1 | 9/2007 | Xiong et al. |
| 7,379,175 B1 | 5/2008 | Stokowski et al. |
| 7,383,156 B2 | 6/2008 | Matsusita et al. |
| 7,386,839 B1 | 6/2008 | Golender et al. |
| 7,388,979 B2 | 6/2008 | Sakai et al. |
| 7,418,124 B2 | 8/2008 | Peterson et al. |
| 7,424,145 B2 | 9/2008 | Horie et al. |
| 7,440,093 B1 | 10/2008 | Xiong et al. |
| 7,570,796 B2 | 8/2009 | Zafar et al. |
| 7,676,077 B2 | 3/2010 | Kulkarni et al. |
| 7,683,319 B2 | 3/2010 | Makino et al. |
| 7,738,093 B2 | 6/2010 | Alles et al. |
| 7,739,064 B1 | 6/2010 | Ryker et al. |
| 7,752,584 B2 | 7/2010 | Yang |
| 7,760,929 B2 | 7/2010 | Orbon et al. |
| 7,769,225 B2 | 8/2010 | Kekare et al. |
| 7,774,153 B1 | 8/2010 | Smith |
| 7,877,722 B2 * | 1/2011 | Duffy et al. ............ 716/55 |
| 7,890,917 B1 | 2/2011 | Young et al. |
| 7,904,845 B2 | 3/2011 | Fouquet et al. |
| 7,968,859 B2 | 6/2011 | Young et al. |
| 8,041,103 B2 | 10/2011 | Kulkarni et al. |
| 8,073,240 B2 * | 12/2011 | Fischer et al. ............ 382/145 |
| 8,112,241 B2 | 2/2012 | Xiong |
| 8,126,255 B2 | 2/2012 | Bhaskar et al. |
| 8,204,297 B1 | 6/2012 | Xiong et al. |
| 8,775,101 B2 * | 7/2014 | Huang et al. ............ 702/40 |
| 2001/0017694 A1 | 8/2001 | Oomori et al. |
| 2001/0019625 A1 | 9/2001 | Kenan et al. |
| 2001/0022858 A1 | 9/2001 | Komiya et al. |
| 2001/0043735 A1 | 11/2001 | Smargiassi et al. |
| 2002/0010560 A1 | 1/2002 | Balachandran |
| 2002/0019729 A1 | 2/2002 | Chang et al. |
| 2002/0026626 A1 | 2/2002 | Randall et al. |
| 2002/0033449 A1 | 3/2002 | Nakasuji et al. |
| 2002/0035461 A1 | 3/2002 | Chang et al. |
| 2002/0035641 A1 | 3/2002 | Kurose et al. |
| 2002/0035717 A1 | 3/2002 | Matsuoka |
| 2002/0054291 A1 | 5/2002 | Tsai et al. |
| 2002/0088951 A1 | 7/2002 | Chen |
| 2002/0090746 A1 | 7/2002 | Xu et al. |
| 2002/0134936 A1 | 9/2002 | Matsui et al. |
| 2002/0144230 A1 | 10/2002 | Rittman |
| 2002/0145734 A1 | 10/2002 | Watkins et al. |
| 2002/0164065 A1 | 11/2002 | Cai et al. |
| 2002/0168099 A1 | 11/2002 | Noy |
| 2002/0176096 A1 | 11/2002 | Sentoku et al. |
| 2002/0181756 A1 | 12/2002 | Shibuya et al. |
| 2002/0186878 A1 | 12/2002 | Hoon et al. |
| 2002/0192578 A1 | 12/2002 | Tanaka et al. |
| 2003/0004699 A1 | 1/2003 | Choi et al. |
| 2003/0014146 A1 | 1/2003 | Fujii et al. |
| 2003/0017664 A1 | 1/2003 | Pnueli et al. |
| 2003/0022401 A1 | 1/2003 | Hamamatsu et al. |
| 2003/0033046 A1 | 2/2003 | Yoshitake et al. |
| 2003/0048458 A1 | 3/2003 | Mieher et al. |
| 2003/0048939 A1 | 3/2003 | Lehman |
| 2003/0057971 A1 | 3/2003 | Nishiyama et al. |
| 2003/0076989 A1 | 4/2003 | Maayah et al. |
| 2003/0086081 A1 | 5/2003 | Lehman |

(56) References Cited

U.S. PATENT DOCUMENTS

| | | | |
|---|---|---|---|
| 2003/0094572 A1 | 5/2003 | Matsui et al. |
| 2003/0098805 A1 | 5/2003 | Bizjak |
| 2003/0128870 A1 | 7/2003 | Pease et al. |
| 2003/0138138 A1 | 7/2003 | Vacca et al. |
| 2003/0138978 A1 | 7/2003 | Tanaka et al. |
| 2003/0169916 A1 | 9/2003 | Hayashi et al. |
| 2003/0173516 A1 | 9/2003 | Takane et al. |
| 2003/0192015 A1 | 10/2003 | Liu |
| 2003/0207475 A1 | 11/2003 | Nakasuji et al. |
| 2003/0223639 A1 | 12/2003 | Shlain et al. |
| 2003/0226951 A1 | 12/2003 | Ye et al. |
| 2003/0227620 A1 | 12/2003 | Yokoyama et al. |
| 2003/0228714 A1 | 12/2003 | Smith et al. |
| 2003/0229410 A1 | 12/2003 | Smith et al. |
| 2003/0229412 A1 | 12/2003 | White et al. |
| 2003/0229868 A1 | 12/2003 | White et al. |
| 2003/0229875 A1 | 12/2003 | Smith et al. |
| 2003/0229880 A1 | 12/2003 | White et al. |
| 2003/0229881 A1 | 12/2003 | White et al. |
| 2003/0237064 A1 | 12/2003 | White et al. |
| 2004/0030430 A1 | 2/2004 | Matsuoka |
| 2004/0032908 A1 | 2/2004 | Hagai et al. |
| 2004/0049722 A1 | 3/2004 | Matsushita |
| 2004/0052411 A1 | 3/2004 | Qian et al. |
| 2004/0057611 A1 | 3/2004 | Lee et al. |
| 2004/0066506 A1 | 4/2004 | Elichai et al. |
| 2004/0091142 A1 | 5/2004 | Peterson et al. |
| 2004/0094762 A1 | 5/2004 | Hess et al. |
| 2004/0098216 A1 | 5/2004 | Ye et al. |
| 2004/0102934 A1 | 5/2004 | Chang |
| 2004/0107412 A1 | 6/2004 | Pack et al. |
| 2004/0119036 A1 | 6/2004 | Ye et al. |
| 2004/0120569 A1 | 6/2004 | Hung et al. |
| 2004/0133369 A1 | 7/2004 | Pack et al. |
| 2004/0147121 A1 | 7/2004 | Nakagaki et al. |
| 2004/0174506 A1 | 9/2004 | Smith |
| 2004/0179738 A1 | 9/2004 | Dai et al. |
| 2004/0199885 A1 | 10/2004 | Lu et al. |
| 2004/0223639 A1 | 11/2004 | Sato |
| 2004/0228515 A1 | 11/2004 | Okabe et al. |
| 2004/0234120 A1 | 11/2004 | Honda et al. |
| 2004/0243320 A1 | 12/2004 | Chang et al. |
| 2004/0246476 A1 | 12/2004 | Bevis et al. |
| 2004/0254752 A1 | 12/2004 | Wisniewski et al. |
| 2005/0004774 A1 | 1/2005 | Volk et al. |
| 2005/0008218 A1 | 1/2005 | O'Dell et al. |
| 2005/0010890 A1 | 1/2005 | Nehmadi et al. |
| 2005/0013474 A1 | 1/2005 | Sim |
| 2005/0062962 A1 | 3/2005 | Fairley et al. |
| 2005/0069217 A1 | 3/2005 | Mukherjee |
| 2005/0117796 A1 | 6/2005 | Matsui et al. |
| 2005/0132306 A1 | 6/2005 | Smith et al. |
| 2005/0141764 A1 | 6/2005 | Tohyama et al. |
| 2005/0166174 A1 | 7/2005 | Ye et al. |
| 2005/0184252 A1 | 8/2005 | Ogawa et al. |
| 2005/0190957 A1 | 9/2005 | Cai et al. |
| 2005/0198602 A1 | 9/2005 | Brankner |
| 2006/0000964 A1 | 1/2006 | Ye et al. |
| 2006/0036979 A1 | 2/2006 | Zurbrick et al. |
| 2006/0038986 A1 | 2/2006 | Honda et al. |
| 2006/0048089 A1 | 3/2006 | Schwarzband |
| 2006/0051682 A1 | 3/2006 | Hess et al. |
| 2006/0062445 A1 | 3/2006 | Verma et al. |
| 2006/0066339 A1 | 3/2006 | Rajski et al. |
| 2006/0082763 A1 | 4/2006 | Teh et al. |
| 2006/0159333 A1 | 7/2006 | Ishikawa |
| 2006/0161452 A1 | 7/2006 | Hess |
| 2006/0193506 A1 | 8/2006 | Dorphan et al. |
| 2006/0193507 A1 | 8/2006 | Sali et al. |
| 2006/0236294 A1 | 10/2006 | Saidin et al. |
| 2006/0236297 A1 | 10/2006 | Melvin et al. |
| 2006/0239536 A1 | 10/2006 | Shibuya et al. |
| 2006/0265145 A1 | 11/2006 | Huet et al. |
| 2006/0266243 A1 | 11/2006 | Percin et al. |
| 2006/0269120 A1 | 11/2006 | Nehmadi et al. |
| 2006/0273242 A1 | 12/2006 | Hunsche et al. |
| 2006/0273266 A1 | 12/2006 | Preil et al. |
| 2006/0277520 A1 | 12/2006 | Gennari |
| 2006/0291714 A1 | 12/2006 | Wu et al. |
| 2006/0292463 A1 | 12/2006 | Best et al. |
| 2007/0002322 A1 | 1/2007 | Borodovsky et al. |
| 2007/0011628 A1 | 1/2007 | Ouali et al. |
| 2007/0013901 A1 | 1/2007 | Kim et al. |
| 2007/0019171 A1 | 1/2007 | Smith |
| 2007/0019856 A1 | 1/2007 | Furman et al. |
| 2007/0031745 A1 | 2/2007 | Ye et al. |
| 2007/0032896 A1 | 2/2007 | Ye et al. |
| 2007/0035322 A1 | 2/2007 | Kang et al. |
| 2007/0035712 A1 | 2/2007 | Gassner et al. |
| 2007/0035728 A1 | 2/2007 | Kekare et al. |
| 2007/0052963 A1 | 3/2007 | Orbon et al. |
| 2007/0064995 A1 | 3/2007 | Oaki et al. |
| 2007/0133860 A1 | 6/2007 | Lin et al. |
| 2007/0156379 A1 | 7/2007 | Kulkarni et al. |
| 2007/0230770 A1 | 10/2007 | Kulkarni et al. |
| 2007/0248257 A1 | 10/2007 | Bruce et al. |
| 2007/0280527 A1 | 12/2007 | Almogy et al. |
| 2007/0288219 A1 | 12/2007 | Zafar et al. |
| 2008/0013083 A1 | 1/2008 | Kirk et al. |
| 2008/0015802 A1 | 1/2008 | Urano et al. |
| 2008/0016481 A1 | 1/2008 | Matsuoka et al. |
| 2008/0018887 A1 | 1/2008 | Chen et al. |
| 2008/0049994 A1 | 2/2008 | Rognin et al. |
| 2008/0058977 A1 | 3/2008 | Honda |
| 2008/0072207 A1 | 3/2008 | Verma et al. |
| 2008/0081385 A1 | 4/2008 | Marella et al. |
| 2008/0163140 A1 | 7/2008 | Fouquet et al. |
| 2008/0167829 A1 | 7/2008 | Park et al. |
| 2008/0250384 A1 | 10/2008 | Duffy et al. |
| 2008/0295047 A1 | 11/2008 | Nehmadi et al. |
| 2008/0295048 A1 | 11/2008 | Nehmadi et al. |
| 2008/0304056 A1 | 12/2008 | Alles et al. |
| 2009/0024967 A1 | 1/2009 | Su et al. |
| 2009/0037134 A1* | 2/2009 | Kulkarni et al. ............... 702/127 |
| 2009/0041332 A1 | 2/2009 | Bhaskar et al. |
| 2009/0043527 A1 | 2/2009 | Park et al. |
| 2009/0055783 A1 | 2/2009 | Florence et al. |
| 2009/0067703 A1 | 3/2009 | Lin et al. |
| 2009/0080759 A1 | 3/2009 | Bhaskar et al. |
| 2009/0210183 A1 | 8/2009 | Rajski et al. |
| 2009/0257645 A1 | 10/2009 | Chen et al. |
| 2009/0284733 A1 | 11/2009 | Wallingford et al. |
| 2009/0290782 A1 | 11/2009 | Regensburger |
| 2009/0299681 A1 | 12/2009 | Chen et al. |
| 2009/0323052 A1 | 12/2009 | Silberstein et al. |
| 2010/0142800 A1 | 6/2010 | Tung-Sing Pak et al. |
| 2010/0146338 A1 | 6/2010 | Schalick et al. |
| 2010/0150429 A1 | 6/2010 | Jau et al. |
| 2010/0188657 A1* | 7/2010 | Chen et al. ............... 356/237.5 |
| 2010/0226562 A1 | 9/2010 | Wu et al. |
| 2011/0013825 A1 | 1/2011 | Shibuya et al. |
| 2011/0052040 A1 | 3/2011 | Kuan |
| 2011/0184662 A1 | 7/2011 | Badger et al. |
| 2011/0251713 A1 | 10/2011 | Teshima et al. |
| 2011/0276935 A1 | 11/2011 | Fouquet et al. |
| 2011/0311126 A1 | 12/2011 | Sakai et al. |
| 2012/0308112 A1 | 12/2012 | Hu et al. |
| 2012/0319246 A1 | 12/2012 | Tan et al. |
| 2013/0009989 A1 | 1/2013 | Chen et al. |
| 2013/0027196 A1 | 1/2013 | Yankun et al. |
| 2013/0336575 A1 | 12/2013 | Dalla-Torre et al. |

FOREIGN PATENT DOCUMENTS

| | | |
|---|---|---|
| CN | 1646896 | 7/2005 |
| EP | 0032197 | 7/1981 |
| EP | 0370322 | 5/1990 |
| EP | 1061358 | 12/2000 |
| EP | 1061571 | 12/2000 |
| EP | 1065567 | 1/2001 |
| EP | 1066925 | 1/2001 |
| EP | 1069609 | 1/2001 |
| EP | 1093017 | 4/2001 |
| EP | 1329771 | 7/2003 |

(56) References Cited

FOREIGN PATENT DOCUMENTS

| | | |
|---|---|---|
| EP | 1480034 | 11/2004 |
| EP | 1696270 | 8/2006 |
| JP | 7-159337 | 6/1995 |
| JP | 2002-071575 | 3/2002 |
| JP | 2002-365235 | 12/2002 |
| JP | 2003-215060 | 7/2003 |
| JP | 2004-045066 | 2/2004 |
| JP | 2005-283326 | 10/2005 |
| JP | 2007-234798 | 9/2007 |
| JP | 2009-122046 | 6/2009 |
| JP | 2010-256242 | 11/2010 |
| JP | 2012-225768 | 11/2012 |
| KR | 10-2001-0007394 | 1/2001 |
| KR | 10-2001-0037026 | 5/2001 |
| KR | 10-2001-0101697 | 11/2001 |
| KR | 10-2003-0055848 | 7/2003 |
| KR | 10-2006-0075691 | 7/2005 |
| KR | 10-2005-0092053 | 9/2005 |
| KR | 10-2006-0124514 | 12/2006 |
| KR | 10-0696276 | 3/2007 |
| KR | 10-2010-0061018 | 6/2010 |
| KR | 10-2012-0068128 | 6/2012 |
| WO | 98/57358 | 12/1998 |
| WO | 99/22310 | 5/1999 |
| WO | 99/25004 | 5/1999 |
| WO | 99/59200 | 5/1999 |
| WO | 99/38002 | 7/1999 |
| WO | 99/41434 | 8/1999 |
| WO | 00/03234 | 1/2000 |
| WO | 00/36525 | 6/2000 |
| WO | 00/55799 | 9/2000 |
| WO | 00/68884 | 11/2000 |
| WO | 00/70332 | 11/2000 |
| WO | 01/09566 | 2/2001 |
| WO | 01/40145 | 6/2001 |
| WO | 03/104921 | 12/2003 |
| WO | 2004/027684 | 4/2004 |
| WO | 20041097903 | 11/2004 |
| WO | 2006/012388 | 2/2006 |
| WO | 2006/063268 | 6/2006 |
| WO | 2009/152046 | 9/2009 |
| WO | 2010/093733 | 8/2010 |

OTHER PUBLICATIONS

Liu, "Robust Image Segmentation Using Local Median," Proceedings of the 3rd Canadian Conference on Computer and Robot Vision (CRV'06) 0-7695-2542-3/06, 2006 IEEE, 7 pages total.

International Search Report and Written Opinion for PCT/US2014/010089 mailed Apr. 30, 2014.

U.S. Appl. No. 60/681,095, filed May 13, 2005 by Nehmadi et al.

U.S. Appl. No. 60/684,360, filed May 24, 2005 by Nehmadi et al.

U.S. Appl. No. 13/652,377, filed Oct. 15, 2012 by Wu et al.

Allan et al., "Critical Area Extraction for Soft Fault Estimation," IEEE Transactions on Semiconductor Manufacturing, vol. 11, No. 1, Feb. 1998.

Barty et al., "Aerial Image Microscopes for the inspection of defects in EUV masks," Proceedings of SPIE, vol. 4889, 2002, pp. 1073-1084.

Budd et al., "A New Mask Evaluation Tool, the Microlithography Simulation Microscope Aerial Image Measurement System," SPIE vol. 2197, 1994, pp. 530-540.

Cai et al., "Enhanced Dispositioning of Reticle Defects Using the Virtual Stepper With Automoated Defect Severity Scoring," Proceedings of the SPIE, vol. 4409, Jan. 2001, pp. 467-478.

Comizzoli, "Uses of Corona Discharges in the Semiconductor Industry," J. Electrochem. Soc., 1987, pp. 424-429.

Contactless Electrical Equivalent Oxide Thickness Measurement, IBM Technical Disclosure Bulletin, vol. 29, No. 10, 1987, pp. 4622-4623.

Contactless Photovoltage vs. Bias Method for Determining Flat-Band Voltage, IBM Technical Disclosure Bulletin, vol. 32, vol. 9A, 1990, pp. 14-17.

Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.

Diebold et al., "Characterization and produiction metrology of thin transistor gate oxide films," Materials Science in Semiconductor Processing 2, 1999, pp. 103-147.

Dirksen et al., "Impact of high order aberrations on the performance of the aberration monitor," Proc. Of SPIE vol. 4000, Mar. 2000, pp. 9-17.

Dirksen et al., "Novel aberration monitor for optical lithography," Proc. Of SPIE vol. 3679, Jul. 1999, pp. 77-86.

Garcia et al., "New Die to Database Inspection Algorithm for Inspection of 90-nm Node Reticles," Proceedings of SPIE, vol. 5130, 2003, pp. 364-374.

Granik et al., "Sub-resolution process windows and yield estimation technique based on detailed full-chip CD simulation," Mentor Graphics, Sep. 2000, 5 pages.

Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.

Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992, No. 1, 2005, p. 6.

Huang et al., "Using Design Based Binning to Improve Defect Excursion Control for 45nm Production," IEEE, International Symposium on Semiconductor Manufacturing, Oct. 2007, pp. 1-3.

Hung et al., Metrology Study of Sub 20 Angstrom oxynitride by Corona-Oxide-Silicon (COS) and Conventional C-V Approaches, 2002, Mat. Res. Soc. Symp. Proc., vol. 716, pp. 119-124.

Karklin et al., "Automatic Defect Severity Scoring for 193 nm Reticle Defect Inspection," Proceedings of SPIE—The International Society for Optical Engineering, 2001, vol. 4346, No. 2, pp. 898-906.

Lo et al., "Identifying Process Window Marginalities of Reticle Designs for 0.15/0.13 µm Technologies," Proceedings of SPIE vol. 5130, 2003, pp. 829-837.

Lorusso et al. "Advanced DFM Applns. Using design-based metrology on CDSEM," SPIE vol. 6152, Mar. 27, 2006.

Lu et al., "Application of Simulation Based Defect Printability Analysis for Mask Qualification Control," Proceedings of SPIE, vol. 5038, 2003, pp. 33-40.

Mack, "Lithographic Simulation: A Review," Proceedings of SPIE vol. 4440, 2001, pp. 59-72.

Martino et al., "Application of the Aerial Image Measurement System (AIMS(TM)) to the Analysis of Binary Mask Imaging and Resolution Enhancement Techniques," SPIE vol. 2197, 1994, pp. 573-584.

Miller, "A New Approach for Measuring Oxide Thickness," Semiconductor International, Jul. 1995, pp. 147-148.

Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.

Numerical Recipes in C. The Art of Scientific Computing, 2nd Ed., © Cambridge University Press 1988, 1992, p. 683.

O'Gorman et al., "Subpixel Registration Using a Concentric Ring Fiducial," Proceedings of the International Conference on Pattern Recognition, vol. ii, Jun. 16, 1990, pp. 249-253.

Otsu, "A Threshold Selection Method from Gray-Level Histograms," IEEE Transactions on Systems, Man, and Cybernetics, vol. SMC-9, No. 1, Jan. 1979, pp. 62-66.

Pang et al., "Simulation-based Defect Printability Analysis on Alternating Phase Shifting Masks for 193 nm Lithography," Proceedings of SPIE, vol. 4889, 2002, pp. 947-954.

Pettibone et al., "Wafer Printability Simulation Accuracy Based on UV Optical Inspection Images of Reticle Defects," Proceedings of SPIE—The International Society for Optical Engineering 1999 Society of Photo-Optical Instrumentation Engineers, vol. 3677, No. II, 1999, pp. 711-720.

Phan et al., "Comparison of Binary Mask Defect Printability Analysis Using Virtual Stepper System and Aerial Image Microscope Sys-

(56) References Cited

OTHER PUBLICATIONS tem," Proceedings of SPIE—The International Society for Optical Engineering 1999 Society of Photo-Optical Instrumentation Engineers, vol. 3873, 1999, pp. 681-692.

Sahouria et al., "Full-chip Process Simulation for Silicon DRC," Mentor Graphics, Mar. 2000, 6 pages.

Sato et al., "Defect Criticality Index (DCI): A new methodology to significantly improve DOI sampling rate in a 45nm production environment," Metrology, Inspection, and Process Control for Microlithography XXII, Proc. Of SPIE vol. 6922, 692213 (2008), pp. 1-9.

Schroder et al., Corona-Oxide-Semiconductor Device Characterization, 1998, Solid-State Electronics, vol. 42, No. 4, pp. 505-512.

Schroder, "Surface voltage and surface photovoltage: history, theory and applications," Measurement Science and Technology, vol. 12, 2001, pp. R16-31.

Schroder, Contactless Surface Charge Semiconductor Characterization, Apr. 2002, Materials Science and Engineering B, vol. 91-92, pp. 196-228.

Schurz et al., "Simulation Study of Reticle Enhancement Technology Applications for 157 nm Lithography," SPIE vol. 4562, 2002, pp. 902-913.

Svidenko et al. "Dynamic Defect-Limited Yield Prediction by Criticality Factor," ISSM Paper: YE-O-157, 2007.

Tang et al., "Analyzing Volume Diagnosis Results with Statistical Learning for Yield Improvement" 12th IEEE European Test Symposium, Freiburg 2007, IEEE European, May 20-24, 2007, pp. 145-150.

Verkuil et al., "A Contactless Alternative to MOS Charge Measurements by Means of a Corona-Oxide-Semiconductor (COS) Technique," Electrochem. Soc. Extended Abstracts, 1988, vol. 88-1, No. 169, pp. 261-262.

Verkuil, "Rapid Contactless Method for Measuring Fixed Oxide Charge Associated with Silicon Processing," IBM Technical Disclosure Bulletin, vol. 24, No. 6, 1981, pp. 3048-3053.

Volk et al. "Investigation of Reticle Defect Formation at DUV Lithography," 2002, BACUS Symposium on Photomask Technology.

Volk et al. "Investigation of Reticle Defect Formation at DUV Lithography," 2003, IEEE/Semi Advanced Manufacturing Conference, pp. 29-35.

Volk et al., "Investigation of Smart Inspection of Critical Layer Reticles using Additional Designer Data to Determine Defect Significance," Proceedings of SPIE vol. 5256, 2003, pp. 489-499.

Weinberg, "Tunneling of Electrons from Si into Thermally Grown $SiO_2$," Solid-State Electronics, 1977, vol. 20, pp. 11-18.

Weinzierl et al., "Non-Contact Corona-Based Process Control Measurements: Where We've Been, Where We're Headed," Electrochemical Society Proceedings, Oct. 1999, vol. 99-16, pp. 342-350.

Yan et al., "Printability of Pellicle Defects in DUV 0.5 μm Lithography," SPIE vol. 1604, 1991, pp. 106-117.

\* cited by examiner

DETECTING DEFECTS ON A WAFER

BACKGROUND OF THE INVENTION

1. Field of the Invention

This invention generally relates to detecting defects on a wafer. Certain embodiments relate to assigning individual output in raw output for a wafer generated by an inspection system to different segments.

2. Description of the Related Art

The following description and examples are not admitted to be prior art by virtue of their inclusion in this section.

Wafer inspection, using either optical or electron beam technologies, is an important technique for debugging semiconductor manufacturing processes, monitoring process variations, and improving production yield in the semiconductor industry. With the ever decreasing scale of modern integrated circuits (ICs) as well as the increasing complexity of the manufacturing process, inspection becomes more and more difficult.

In each processing step performed on a semiconductor wafer, the same circuit pattern is printed in each die on the wafer. Most wafer inspection systems take advantage of this fact and use a relatively simple die-to-die comparison to detect defects on the wafer. However, the printed circuit in each die may include many areas of patterned features that repeat in the x or y direction such as the areas of DRAM, SRAM, or FLASH. This type of area is commonly referred to as an array area (the rest of the areas are called random or logic areas). To achieve better sensitivity, advanced inspection systems employ different strategies for inspecting the array areas and the random or logic areas.

To set up a wafer inspection process for array inspection, many currently used inspection systems require users to manually set up regions of interest (ROI) and apply the same set of parameters for defect detection in the same ROI. However, this method of set up is disadvantageous for a number of reasons. For example, as design rules shrink, region definition can be much more complicated and much smaller in area. With the limitations on stage accuracy and resolution of the inspection system, manual set up of ROI will become impossible eventually. On the other hand, if the distance between page breaks is larger than Fourier filtering can perform, the page break will not be suppressed in the array region.

In another method, intensity is used as a feature of segmentation to group similar intensity pixels together. Then, the same set of parameters is applied for the same group of pixels (intensity-based). However, this method also has a number of disadvantages. For example, an intensity-based segmentation algorithm can be used when a geometry feature scatters uniformly. Often, however, this is not enough. Therefore, other property-based segmentation is needed.

Accordingly, it would be advantageous to develop methods and systems for detecting defects on a wafer that can achieve better detection of defects by utilizing the knowledge that defects of interest and nuisance/noise reside in different segments geometrically.

SUMMARY OF THE INVENTION

The following description of various embodiments is not to be construed in any way as limiting the subject matter of the appended claims.

One embodiment relates to a computer-implemented method for detecting defects on a wafer. The computer-implemented method includes acquiring first raw output for a wafer generated using a first optics mode of an inspection system and second raw output generated for the wafer using a second optics mode of the inspection system. The method also includes identifying one or more characteristics of the first raw output that correspond to one or more geometrical characteristics of patterned features formed on the wafer. In addition, the method includes assigning individual output in the second raw output to different segments based on the identified one or more characteristics of the first raw output and based on the individual output in the second raw output and individual output in the first raw output that were generated at substantially the same locations on the wafer such that the one or more geometrical characteristics of the patterned features that correspond to each of the different segments in the second raw output are different. The method further includes separately assigning one or more defect detection parameters to the different segments. Furthermore, the method includes applying the assigned one or more defect detection parameters to the individual output in the second raw output assigned to the different segments to thereby detect defects on the wafer.

Each of the steps of the computer-implemented method described above may be performed as described further herein. The computer-implemented method described above may include any other step(s) of any other method(s) described herein. The computer-implemented method described above may be performed using any of the systems described herein.

Another embodiment relates to a non-transitory computer-readable medium storing program instructions executable on a computer system for performing a method for detecting defects on a wafer. The method includes the steps of the computer-implemented method described above. The non-transitory computer-readable medium may be further configured as described herein. The steps of the method may be performed as described further herein. In addition, the method for which the program instructions are executable may include any other step(s) of any other method(s) described herein.

An additional embodiment relates to a system configured to detect defects on a wafer. The system includes an inspection subsystem configured to generate first raw output for a wafer by scanning the wafer using a first optics mode of the inspection subsystem and to generate second raw output for the wafer by scanning the wafer using a second optics mode of the inspection subsystem. The system also includes a computer subsystem configured to acquire the first and second raw output. The computer subsystem is also configured to identify one or more characteristics of the first raw output that correspond to one or more geometrical characteristics of patterned features formed on the wafer. In addition, the computer subsystem is configured to assign individual output in the second raw output to different segments based on the identified one or more characteristics of the first raw output and based on the individual output in the second raw output and individual output in the first raw output that were generated at substantially the same locations on the wafer such that the one or more geometrical characteristics of the patterned features that correspond to each of the different segments in the second raw output are different. The computer subsystem is further configured to separately assign one or more defect detection parameters to the different segments and apply the assigned one or more defect detection parameters to the individual output in the second raw output assigned to the different segments to thereby detect defects on the wafer. The system may be further configured as described herein.

BRIEF DESCRIPTION OF THE DRAWINGS

Other objects and advantages of the invention will become apparent upon reading the following detailed description and upon reference to the accompanying drawings in which.

Figure 1:
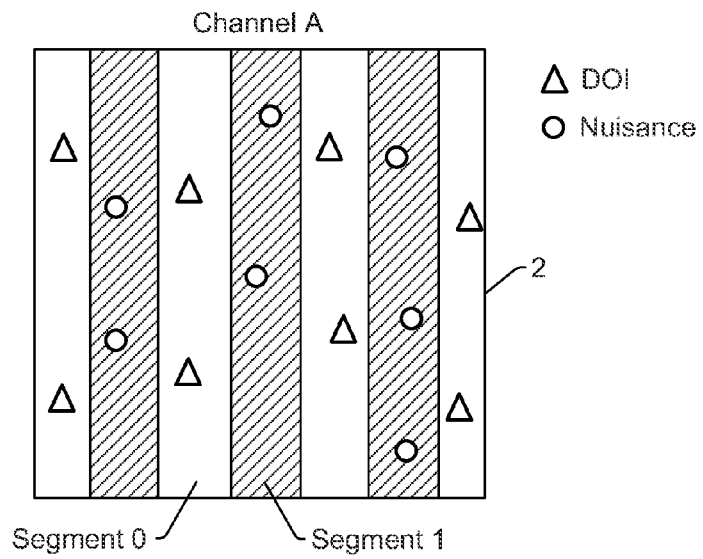
FIG. 1 is a schematic diagram illustrating one example of a method for detecting defects on a wafer in which segmentation and defect detection are performed using raw output generated by the same channel of an inspection system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a computer-implemented method for detecting defects on a wafer. The computer-implemented method includes acquiring first raw output for a wafer generated using a first optics mode of an inspection system and second raw output generated for the wafer using a second optics mode of the inspection system, as shown in step 40 of FIG. 5. Acquiring the first and second raw output for the wafer may be performed using the inspection system. For example, acquiring the first and second raw output may include using the inspection system to scan light over the wafer and to generate first and second raw output responsive to light scattered and/or reflected from the wafer detected by the inspection system during scanning. In this manner, acquiring the first and second raw output may include scanning the wafer. However, acquiring, the first and second raw output does not necessarily include scanning the wafer. For example, acquiring the first and second raw output may include acquiring the first and second raw output from a storage medium in which the first and second raw output has been stored (e.g., by the inspection system). Acquiring the first and second raw output from the storage medium may be performed in any suitable manner, and the storage medium from which the output is acquired may include any of the storage media described herein. In any case, the method includes raw output (e.g., raw data) collection.

In one embodiment, the first and second raw output is responsive to light scattered from the wafer. In particular, the first and second raw output may be responsive to light scattered from the wafer and detected by the inspection system. Alternatively, the first and second raw output may be responsive to light reflected from the wafer and detected by the inspection system. The first and second raw output may include any suitable raw output and may vary depending on the configuration of the inspection system. For example, the first and second raw output may include signals, data, image data, etc. In addition, the first and second raw output may be generally defined as output for at least a portion (e.g., multiple pixels) of the entire output generated for the wafer by the inspection system. Furthermore, the first and second raw output may include all of the raw output generated for the entire wafer by the inspection system, all of the raw output generated for the entire portion of the wafer that is scanned by the inspection system, etc., regardless of whether the raw output corresponds to defects on the wafer.

In contrast, individual output may be generally defined as output for an individual pixel of the entire output generated for the wafer by the inspection system. Therefore, the first and second raw output may each include multiple individual output. In other words, the individual output may be output separately generated for different locations on the wafer. For example, the individual output may include individual, discrete output generated for different locations on the wafer. In particular, the different locations may correspond to different "inspection points" on the wafer. In other words, the different locations may correspond to locations on the wafer for which output is separately generated by the inspection system. In this manner, the different locations may correspond to each location on the wafer at which a "measurement" is performed by the inspection system. As such, the different locations may vary depending on the configuration of the inspection system (e.g., the manner in which the inspection system generates output for the wafer). The individual output includes individual output that does and does not correspond to defects on the wafer.

The inspection system may be configured as described herein. For example, the inspection system may be configured for dark field (DF) inspection of the wafer. In this manner, the inspection system may include a DF inspection system. The DF inspection system may be configured as described further herein. In another example, the inspection system may be configured for bright field (BF) inspection of the wafer. In this manner, the inspection system may include a BF inspection system. The BF inspection system may have any suitable configuration known in the art. The inspection system may also be configured for BF and DF inspection. Furthermore, the inspection system may be configured as a scanning electron microscopy (SEM) inspection and review system, and such an inspection system may have any suitable configuration known in the art. In addition, the inspection system may be configured for inspection of patterned wafers and possibly also unpatterned wafers.

In one embodiment, the first and second optics modes are defined by different detectors of the inspection system and the same values for other optical parameters of the inspection system. For example, the inspection system may include multiple detectors (or channels) as shown and described further herein, and the first raw output may be generated using a first of the detectors (or channels) and the second raw output may be generated using a second of the detectors (or channels). In this manner, the first and second raw output may be generated using different detectors of the inspection system. The different detectors may generate the first and second raw output in the same pass substantially simultaneously. The different detectors may be different in that they are physically different detectors that detect light collected at different angles, but otherwise the detectors may have the same configuration (e.g., the same make and model). However, the different detectors may be different in that they are physically different detectors that detect light collected at different angles and have different configurations. In addition, the different detectors are not generally different light sensitive elements of the same detector. For example, the different detectors are not different pixels of the same detector. The other optical parameters of the inspection system may include all or any other optical parameters of the inspection system such as illumination wavelength(s), illumination polarization(s), illumination angle(s), collection angle(s), detection wavelength(s), detection polarization(s), and the like.

In another embodiment, the first and second optics modes are defined by different detectors of the inspection system, one or more different values for one or more optical parameters of the inspection system, and the same values for other optical parameters of the inspection system. The first and second optics modes may be defined by different detectors as described above, and the different detectors may be configured as described above. The one or more optical parameters having one or more different values may be any of the optical parameters described above, and the other optical parameters having the same values may include any of the remaining optical parameters described above. For example, the first and second optics modes may be defined by different detectors, different values of illumination and detection polarization, and the same values for all other optical parameters of the inspection system.

In an additional embodiment, the first and second optics modes are defined by the same detector of the inspection system, one or more different values for one or more optical parameters of the inspection system, and the same values for other optical parameters of the inspection system. In this manner, the first and second optics modes may be defined by the same detector (or channel), which may be configured as shown and described further herein, but different values for at least some of the optical parameters of the inspection system. For example, the first and second optics modes may be defined by the same detector but different values for illumination polarization. The same detector may generate the first and second raw output in the same pass substantially simultaneously or in different passes sequentially (e.g., depending on the different values of the optical parameters and the capability of the detector).

In another embodiment, the first and second optics modes are defined by a combination of the same set of detectors of the inspection system, one or more different values for one or more optical parameters of the inspection system, and the same values for other optical parameters of the inspection system. For example, the first and second optics modes may be defined by the same two detectors, the same three detectors, etc., which may be configured as shown and described herein, but different values for at least some of the optical parameters of the inspection system. In one such example, the first and second optics modes may be defined by the same set of two detectors but different values for illumination polarization. The same detectors may generate the first and second raw output in the same pass substantially simultaneously or in different passes sequentially (e.g., depending on the different values of the optical parameters and the capability of the detectors).

In some embodiments, the first and second optics modes are defined by a combination of a subset of detectors of the inspection system, one or more different values for one or more optical parameters of the inspection system, and the same values for other optical parameters of the inspection system. For example, the first and second optics modes may be defined by the same two detectors, the same three detectors, etc., which do not include all of the detectors in the inspection system and which may be configured as shown and described herein, and different values for at least some of the optical parameters of the inspection system. In one such example, the first and second optics modes may be defined by the same two detectors of the inspection system, but not a third detector of the inspection system, and different values for illumination polarization. The detectors included in the subset may generate the first and second raw output as described above.

Figure 5:
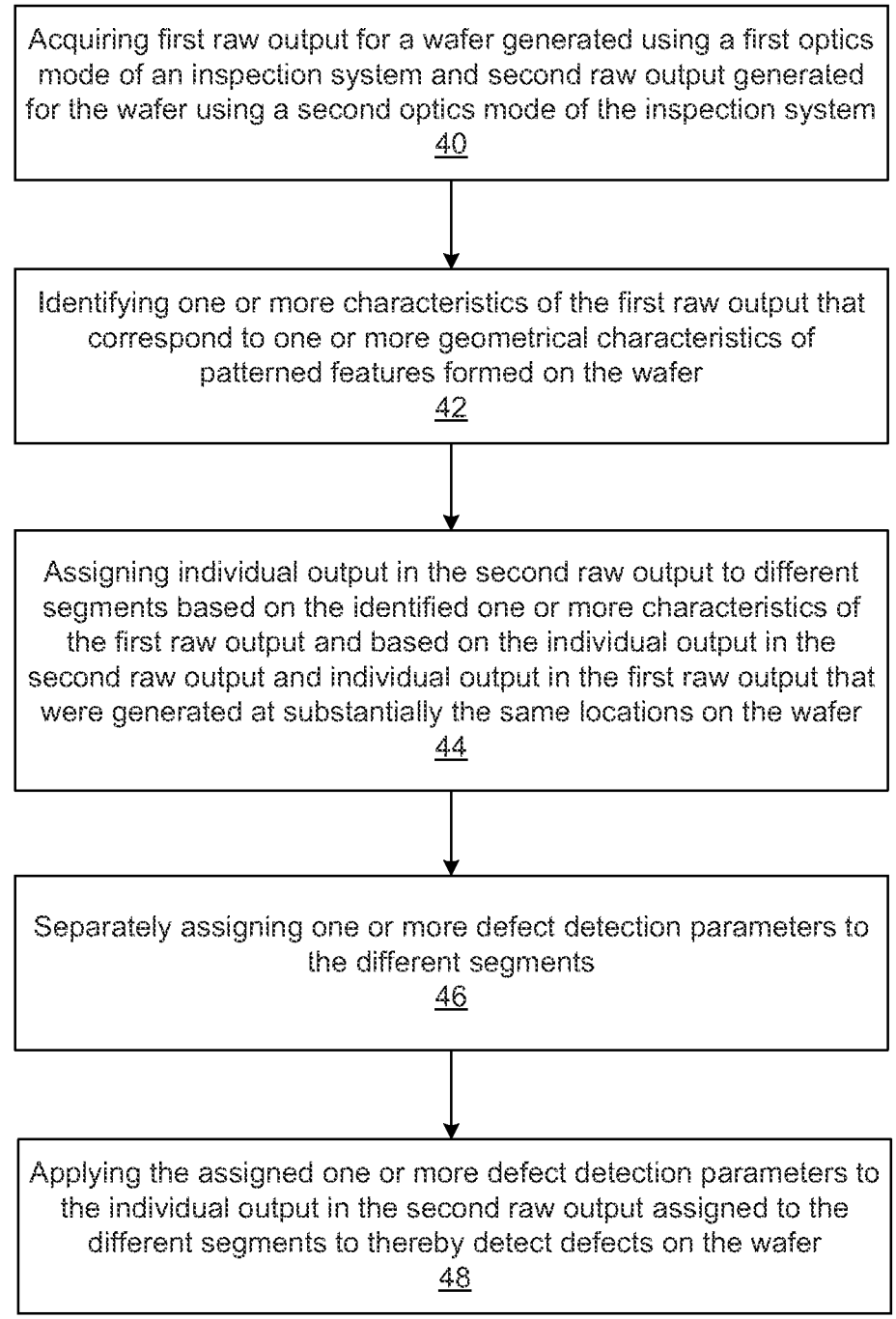
FIG. 5 is a flow chart illustrating one embodiment of a method for detecting defects on a wafer.

The computer-implemented method also includes identifying one or more characteristics of the first raw output that correspond to one or more geometrical characteristics of patterned features formed on the wafer, as shown in step 42 of FIG. 5. In one embodiment, the identified one or more characteristics of the first raw output include projections along lines within the first raw output. A projection can be generally defined as a group, cluster, or summation of individual output that has some pattern within the raw output. For example, projections along horizontal and vertical lines of the first raw output can be gathered. In this manner, x and y projections within the first raw output can be identified that define or correspond to one or more geometrical characteristics of the patterned features. As such, identifying the one or more characteristics of the first raw output may include performing two-dimensional (2D) projection of the first raw output. However, the one or more characteristics of the first raw output that correspond to the one or more geometrical characteristics of patterned features formed on the wafer may include any other characteristic(s) of the first raw output. For example, in another embodiment, the identified one or more characteristics of the first raw output include median intensity of the first raw output that corresponds to the one or more geometrical characteristics of the patterned features. Identifying the one or more characteristics of the first raw output as described above may be performed in any suitable manner using any suitable method and/or algorithm.

In one embodiment, the one or more geometrical characteristics of the patterned features include edges, shape, texture, a mathematical calculation that defines geometry of the patterned features, or some combination thereof. For example, characteristics that can be used for geometric-based segmentation, which may be performed as described further herein, include edges, shape, texture, any mathematical calculation/transformation that defines the geometry, or some combination thereof. Although all patterned features formed on a wafer may have some roughness and therefore some "texture," texture is different than roughness in that roughness is generally used to refer to and describe roughness just on the periphery of patterned features while texture generally refers to the overall texture (e.g., as designed or not) of patterned features. One example of a mathematical calculation/transformation that can be used to define the geometry of the patterned features is a Fourier filtering algorithm, which can be used to describe a relationship between geometry and light scattering. For example, a Fourier filtering algorithm can be used to predict projections in the raw output that will correspond to one or more geometrical characteristics of the patterned features.

In one embodiment, identifying the one or more characteristics of the first raw output is performed based on how a design layout of the patterned features will affect the one or more characteristics of the first raw output. For example, a characteristic that can be used for segmentation, which can be performed as described herein, is the design layout. In particular, the design layout can be used to identify one or more geometrical characteristics of patterned features in the design layout. One or more characteristics (e.g., projections) of the first raw output that will correspond to the one or more identified geometrical characteristics can then be determined (e.g., empirically, theoretically, etc.). In this manner, one or more expected characteristics of the first raw output that will correspond to one or more geometrical characteristics of the patterned features can be determined. Those one or more expected characteristics can then be compared to one or more characteristics of the first raw output in any suitable manner to identify the one or more characteristics of the first raw output that correspond to one or more geometrical characteristics of the patterned features. The design layout used in this step may be acquired in any suitable manner and may have any suitable format.

In another embodiment, identifying the one or more characteristics of the first raw output is performed while acquiring the first and second raw output is being performed. In this manner, identifying the one or more characteristics of the first raw output may be performed on-the-fly as the wafer is being scanned by the inspection system. For example, identifying the one or more characteristics of the first raw output can be performed using first raw output that is acquired for the wafer in the same scan as the second raw output. As such, other steps described herein (e.g., segmentation) that are performed using the one or more identified characteristics of the first raw output may also be performed on-the-fly during acquisition of the first and second raw output for the wafer.

The computer-implemented method also includes assigning individual output in the second raw output to different segments based on the identified one or more characteristics of the first raw output and based on the individual output in the second raw output and individual output in the first raw output that were generated at substantially the same location on the wafer such that the one or more geometrical characteristics of the patterned features that correspond to each of the different segments in the second raw output are different, as shown in step 44 of FIG. 5. In this manner, the embodiments described herein are configured for geometry-based segmentation. More specifically, the embodiments described herein utilize how the geometrical characteristic(s) (e.g., shape) of wafer patterns will affect the first and second raw output and separate the patterns that affect the first and second raw output differently into different segments. In other words, the embodiments described herein utilize how the geometrical characteristic(s) (e.g., shape) of patterns on the wafer will affect the first and second raw output to separate individual output in the second raw output into different segments. For instance, patterned features that have one or more different geometrical characteristics may have different effects on light scattered from the wafer and thereby may have different effects on the first and second raw output generated for the wafer. Those patterned features can be effectively separated into different segments by the embodiments described herein. Assigning the individual output in the second raw output to different segments as described herein can be performed in any suitable manner using any suitable method and/or algorithm. The individual output in the first and second raw output that was generated at substantially the same location on the water may be identified based on wafer position information that comes from wafer alignment and/or registration with a stage of the inspection system.

"Segments" can be generally defined as different portions of an entire range of possible values for the individual output. The segments may be defined based on values for different characteristics of the individual output depending on the defect detection algorithm that uses the segments. For instance, in the multiple die auto-thresholding (MDAT) algorithm, the value for the characteristic of the individual output that is used to define the segments may include median intensity value. In one such illustrative and non-limiting example, if the entire range of median intensity values is from 0 to 255, a first segment may include median intensity values from 0 to 100 and a second segment may include median intensity values from 101 to 255. In this manner, the first segment corresponds to darker areas in the raw output, and the second segment corresponds to brighter areas in the raw output. In some instances, the segments can be defined using one wafer, and for wafers having similar geometry as that one wafer, the predefined segments can be used.

The embodiments described herein are, therefore, configured for segmentation and detecting defects on a wafer using a multiple optics mode (or multi-perspective) architecture. As such, the embodiments described herein provide unique value for defect detection on a multi-channel (or multi-detector) system. For example, the embodiments basically apply information collected from one mode to another mode (having the same or different collector as the one mode). In one such example, it allows detection of defects in one of several channels (or detectors) by utilizing output input information acquired from other channels (or detectors).

In contrast to the embodiments described herein, as shown in FIG. 1, currently used methods for performing segmentation and defect detection use raw output 2 generated by one channel (e.g., Channel A) of an inspection system (not shown in FIG. 1) to generate segments (e.g., Segment 0 and Segment 1) and then using the same raw output to perform defect detection in Segment 0 to detect defects of interest (DOI) while not performing defect detection in Segment 1 such that nuisance defects in Segment 1 are not detected. In this manner, in currently used methods, defect detection and segmentation partition are based on the raw output from the same channel (or detector). As illustrated in FIG. 1, therefore, the currently used methods do divide raw output into segments but the segmentation outlines are based on the same channel as the defect detection channel, meaning defect detection and segmentation partition are based on the raw output information from the same channel. In addition, the currently used methods do not use the segment information generated using any one channel (or detector) for a different channel (or detector).

However, for multi-channel inspectors, there are many cases in which the channel detecting the defects might not have clear separation of the segments while other channels may have clear segment separation but no signal for the defects. When encountering this situation, the currently used methods will have the disadvantage of using segmentation for defect detection based on one channel information.

Figure 2:
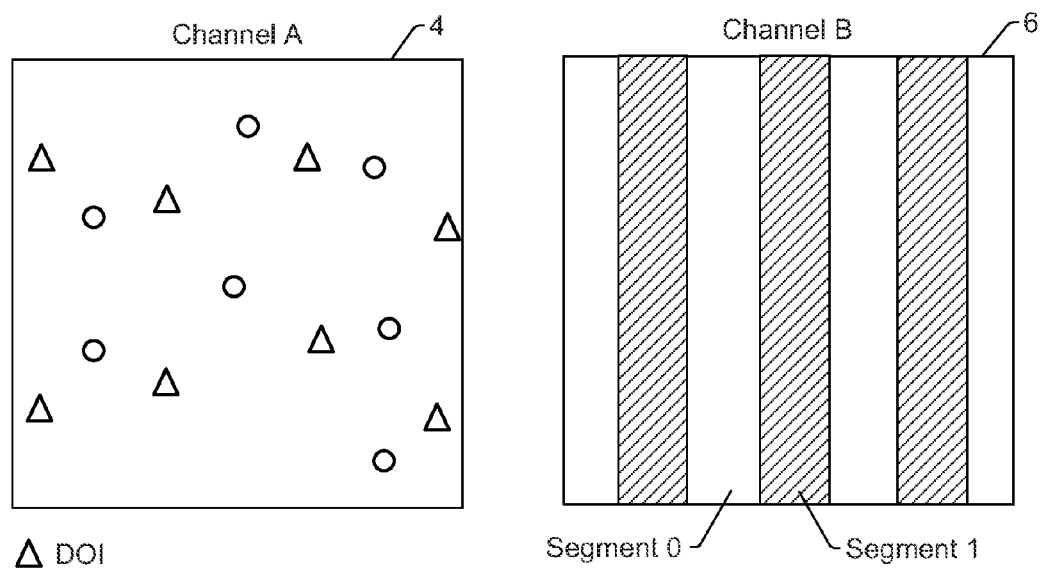
FIG. 2 is a schematic diagram illustrating one embodiment of a method for detecting defects on a wafer in which segmentation and defect detection are performed using raw output generated by different channels of an inspection system.

The embodiments described herein, however, address this issue by sharing segments across channels. For example, the raw output acquired from one detector may be divided into two or more segments based on the geometrical characteristics of patterned features formed on the wafer, then the segment information may be applied to another channel or detector through wafer position information. In one such example, as shown in FIG. 2, raw output 6 generated using one channel (e.g., Channel B) may be used to determine the segments (e.g., Segment 0 and Segment 1). Those segments may then be applied to raw output 4 generated using a different channel (e.g., Channel A) such that DOI can be detected in one of the segments (e.g., Segment 0) while defect detection is not performed in another of the segments (e.g., Segment 1) such that nuisance defects are not detected in that segment. In this manner, defect detection and segmentation partitions can be performed using output generated by different channels (or detectors). As such, segments can be shared across channels or detectors.

The embodiments described herein may be particularly useful in a number of use cases such as copper residue detection on wafers after chemical mechanical planarization of a copper layer has been performed on the wafers. For example, two different channels of the same inspection system may generate raw output for the wafers. Both channels may detect light scattered from the wafer, which may include copper lines with an oxide formed between the copper lines. The DOI in this case may be copper residue on the oxide between the copper lines. One of the channels may produce raw output that can be used to detect such DOI. However, the same channel may detect strong scattering from the copper lines. Therefore, although DOI can be detected using the raw output generated by this channel, the strong scattering from the copper lines becomes the main nuisance source. In other words, while this channel may have good detection of copper residue, the copper line scattering is also strong and becomes the main nuisance source. As such, detecting the copper residue defects using this channel will result in significant nuisance defect detection. Therefore, segmentation between the copper lines and the oxide between the lines is definitely needed for this channel to detect copper residue with a low nuisance rate. However, segmentation separation using this channel may not be ideal and clean, especially for defective dies because the copper residue between the copper lines has almost the same scattering intensity as the copper lines themselves. Therefore, currently used methods of segmentation, in which defect detection and segmentation partitions are based on the same channel, will not work in this case.

Another channel of the inspection system may, however, have no detection of the copper residue DOI but may have clear segment separation between the copper lines and the oxide. Therefore, in the embodiments described herein, the raw output from this channel may be divided into two segments (e.g., copper lines and oxide), then segmentation information may be applied to the raw output generated by the other channel described above through wafer position information. After this has been performed, the other channel described above will have clear segmentation separation, which will enable DOI (copper residue) capture with relatively low nuisance rate.

The segmentation described herein can be projection-based or median intensity-based. Median-based segmentation is basically segmentation based on reference image raw intensity. For median-based segmentation, the first raw output may be divided into two or more segments based on median intensity of the first raw output, then the segment information may be applied to the second channel or detector through wafer position information.

In one embodiment, identifying the one or more characteristics of the first raw output and assigning the individual output in the second raw output to the different segments are performed automatically without user input. For example, the embodiments described herein can utilize the geometrical characteristic(s) (e.g., shape) of patterns on the wafer and projection to automatically separate the individual output in the second raw output into different segments. In this manner, unlike methods that include manually setting up regions of interest (ROI) and applying the same set of parameters for defect detection in the same ROI, as design rules shrink and as the different areas on the wafer to be segmented get smaller, segmentation will not become more complicated using the embodiments described herein. In addition, unlike manual methods, automatically identifying the one or more characteristics of the first raw output and assigning the individual output in the second raw output to the different segments without user input is not affected by inspection system stage accuracy and resolution limitations. Therefore, using the embodiments described herein for segmentation, the inspection system stage accuracy and resolution limitations will not make segmentation impossible.

In another embodiment, assigning the individual output in the second raw output to the different segments is performed without regard to design data associated with the patterned features. For example, although the design layout may be used as described above to determine one or more expected characteristics of the first raw output that will correspond to one or more geometrical characteristics of the patterned features, segmentation is not performed based on the design data itself. In other words, segmentation is based on how the one or more geometrical characteristics of the patterned features will affect the first raw output, but is not based on the one or more geometrical characteristics of the patterned features themselves. In this manner, unlike other methods and systems that segment raw output based on the design data associated with patterned features, performing segmentation based on how the one or more geometrical characteristics of the patterned features will affect the first raw output may result in patterned features associated with different design data, different electrical functions, different electrical characteristics, different criticalities to the performance of the device being formed using the patterned features, etc. being assigned to the same segment if those patterned features will affect the first raw output in the same manner. For example, performing segmentation based on how the geometrical characteristic(s) will affect characteristic(s) (e.g., intensity) of the first raw output instead of the geometry itself may result in patterned features that produce significant noise in the first raw output being assigned to the same segment regardless of the design data associated with those patterned features and other patterned features that produce negligible noise in the first raw output being assigned to a different segment again regardless of the design data associated with those other patterned features. In this manner, high noise patterned features can be segmented together, and low noise patterned features can be segmented together.

In an additional embodiment, assigning the individual output in the second raw output to the different segments is performed without regard to intensity of the individual output in the second raw output. In other words, although the segmentation is performed based on the one or more identified characteristics of the first raw output, which may be identified based on intensity of multiple individual output in the first raw output, the segmentation is not performed based on intensity of the individual output in the first or second raw output itself. For example, projections along lines within the first raw output may include individual output that have a variety and possibly dramatically different intensities. Nevertheless, all of that individual output may correspond to the same one or more geometrical characteristics of patterned features such as page breaks. As such, all of the individual output in the second raw output that corresponds to the same one or more geometrical characteristics of the patterned features can be assigned to the same segment even though all of that individual output may have dramatically different intensities. In this manner, unlike methods for performing segmentation based on the intensity of individual pixels, the segmentation performed by the embodiments described herein will not be affected by non-uniform scattering from the patterned features.

In some embodiments, assigning the individual output in the second raw output to the different segments includes analyzing the identified one or more characteristics of the first raw output and applying thresholds to the individual output of the second raw output. For example, as described above, projections along horizontal and vertical lines in the first raw output can be gathered. The projections can then be analyzed, and thresholds can be set to separate the individual output in the second raw output into different areas of interest (segments). Analyzing the identified one or more characteristics of the first raw output and applying thresholds to the individual output in the second raw output may reduce the number of individual output corresponding to boundary regions from being inappropriately assigned to the segments.

In one embodiment, the one or more geometrical characteristics that correspond to one of the different segments include one or more geometrical characteristics of page breaks, and the one or more geometrical characteristics that correspond to another of the different segments include one or more geometrical characteristics of array areas. Page breaks are generally defined in the art as regions of a die separating substantially continuous regions of physical memory. Each of the continuous regions of physical memory may be commonly referred to as a page frame. Performing segmentation as described herein, one or more characteristics of the first raw output (e.g., the x and/or y projections) that define the geometry for page breaks in array regions can be identified and used to assign individual output in the second raw output corresponding to the page breaks to one segment and to assign individual output in the second raw output corresponding to array regions to a different segment.

In another embodiment, the one or more characteristics of the first raw output that correspond to the one or more geometrical characteristics of some of the patterned features cannot be suppressed by filtering such as optical, mechanical, or electronic filtering systems such as Fourier filtering. For example, unlike some methods for segmentation, even if the distance between page breaks is larger than Fourier filtering can perform, the page break can be suppressed in the array region. In one such example, for some inspection systems, if the width of a page break is about 5 μm and the spacing between page breaks is about 5 μm. Fourier filtering becomes impractical if not impossible while manual set up of ROI also becomes impractical if not impossible. Therefore, the signal (noise) produced in the second raw output by the page breaks may not be suppressed and can thereby reduce the defect detection sensitivity that can be achieved using the second raw output. However, using the embodiments described herein, the individual output in the second raw output that corresponds to the page breaks can be identified (e.g., based on projections within the first raw output), and the individual output in the second raw output that corresponds to the page breaks can be assigned to one segment while other individual output in the second raw output can be assigned to other segments such that as described further herein different sensitivities can be used to detect defects in different segments.

The computer-implemented method further includes separately assigning one or more defect detection parameters to the different segments, as shown in step 46 of FIG. 5. One or more defect detection parameters can be separately assigned to all of the different segments. Therefore, some of the individual output in the second raw output may not be ignored when it comes to defect detection. Instead, defects can be detected using the individual output assigned to all of the different segments. In other words, defects can be detected using all segments of the second raw output. In this manner, different segments can be treated differently with different inspection recipes. The different inspection recipes may be different in the defect detection algorithms that are assigned to the different segments. Alternatively, the different inspection recipes may be different in one or more parameters of the same defect detection algorithm that are assigned to the different segments. The defect detection algorithms that are assigned to the different segments or one or more parameters of which are assigned to the different segments may include any suitable defect detection algorithms. For example, the defect detection algorithm may be a segmented auto-thresholding (SAT) algorithm or an MDAT algorithm. Such defect detection algorithms may be particularly suitable for BF inspection. However, the defect detection algorithm may be a defect detection algorithm that is suitable for DF inspection. For example, the defect detection algorithm may be a FAST algorithm or an HLAT algorithm.

The different inspection recipes may also be different in one or more optical parameters of the inspection system that are used to acquire the second raw output for the wafer. For example, in a multi-pass inspection, different passes may be performed with different values for at least one optical parameter (e.g., polarization, wavelength, angle of illumination, angle of collection, etc.) of the inspection system, and second raw output generated in the different passes may be used to detect defects in different regions of the wafer in which patterned features having one or more different geometrical characteristics are formed. In this manner, regions of the wafer that include patterned features having one or more different geometrical characteristics can be inspected using second raw output generated in different passes of a multi-pass inspection performed using one or more different optical parameters.

In one embodiment, the one or more defect detection parameters include a threshold to be applied to a difference between the individual output in the second raw output and a reference. In this manner, different thresholds can be applied to the difference between the individual output in the second raw output and the reference depending on the segment to which the individual output in the second raw output has been assigned. For example, a reference (such as an 8-bit reference image) may be subtracted from the individual output in the second raw output (such as an 8-bit test image) regardless of the segment to which the individual output in the second raw output has been assigned. The reference may include any suitable reference such as individual output in the second raw output corresponding to a die on the wafer that is different than the die in which the individual output in the second raw output, from which the reference is being subtracted, has been generated, a cell on the wafer that is different than the cell in which the individual output in the second raw output, from which the reference is being subtracted, has been generated, etc. Any individual output in the second raw output having a difference above the assigned threshold may be identified as a defect. In this manner, defects can be detected with different thresholds depending on the segment to which the individual output in the second raw output has been assigned.

In another embodiment, separately assigning the one or more defect detection parameters to the different segments is performed such that defects are detected using the individual output of the second raw output assigned to the different segments with different sensitivities. Therefore, the embodiments described herein can achieve better detection of defects by utilizing the knowledge that DOI and nuisance/noise reside in different segments geometrically. For example, different geometries can exhibit different types of defects. In one such example, in an array pattern region, the first raw output may include alternating line-like patterns of relatively bright individual output and relatively dark individual output. In some such instances, DOI may be located in portions of the second raw output corresponding to portions of the first raw output that include the relatively bright individual output while nuisance defects may be located in portions of the second raw output corresponding to portions of the first raw output that include the relatively dark individual output. In this manner, with segmentation using characteristic(s) that define the geometry (e.g., the x or y projection for page break in the array region), the sensitivity of a detection algorithm can be set up differently for better sensitivity in the array area and less nuisance from the page break. Therefore, the embodiments described herein advantageously allow an automatic way of separating different geometric patterns of the wafer into different segments. This segmentation makes it possible for these areas to be treated differently and better sensitivity can be achieved. Different geometries also scatter light differently. In this manner, some geometries may cause the first raw output to be relatively noisy while other geometries may cause the first raw output to be relatively quiet. However, using only intensity of the individual output of the first raw output for segmentation, individual output corresponding to relatively noisy and relatively quiet regions in the second raw output can be grouped together (e.g., due to poorly defined boundaries). In contrast, in the embodiments described herein, for defects that are located in areas of the wafer that have one or more geometrical characteristics that correspond to less noise in the second raw output, higher sensitivity can be achieved. In addition, for narrow band inspection systems, defects can often be buried in noise since patterns also scatter a significant amount of light. However, the embodiments described herein make it possible to detect those defects that are detuned by noise from nearby patterns.

The computer-implemented method further includes applying the assigned one or more defect detection parameters to the individual output in the second raw output assigned to the different segments to thereby detect defects on the wafer, as shown in step 48 of FIG. 5. As described above, different segments can be treated differently with different inspection recipes. In this manner, applying the assigned one or more defect detection parameters to the individual output in the second raw output may include inspecting segments with different recipes to thereby detect defects on the wafer. For example, the segment to which the individual output in the second raw output has been assigned can be used to determine the threshold that is to be applied to the difference between the individual output in the second raw output and the reference. After determining the segment to which the individual output in the second raw output has been assigned and assigning the one or more defect detection parameters to the different segments, the assigned one or more defect detection parameters can be applied to the individual output in the second raw output assigned to the different segments as would normally be performed.

In one embodiment, acquiring the first and second raw output is performed in one pass of a multi-pass inspection of the wafer, and the computer-implemented method, is not performed for raw output acquired, in another pass of the multi-pass inspection. In this manner, segmentation as described herein may be performed for only one pass of a multi-pass inspection. Raw output acquired in other passes can be used for other purposes. For example, multi-pass inspection may serve the segmentation purpose with one pass having the optimum signal to defects and another pass providing the geometry-based segmentation. In particular, different passes of the multi-pass inspection may be performed with one or more different defect detection parameters and/or one or more different optical parameters such that the raw output and/or the defect, detection results are different for different passes. In one such example, one optical mode used in one pass of the multi-pass inspection may allow segmentation while another optical mode of the inspection system used in another pass of the multi-pass inspection may provide the highest sensitivity to DOI. However, segmentation as described herein may be performed for multiple passes of a multi-pass inspection. For example, in another embodiment, acquiring the first and second raw output is performed in one pass of a multi-pass inspection of the wafer, and the computer-implemented method is performed for raw output acquired in another pass of the multi-pass inspection. The computer-implemented method may be performed with one or more different parameters for the different passes.

In another embodiment, additional defects are detected using the raw output acquired in the other pass, and the method includes combining the defects and the additional defects to generate inspection results for the wafer. For example, as described above, one pass of a multi-pass inspection may be used for segmentation while another pass of the multi-pass inspection may be used to detect DOI with optimum signal. In another example, different passes may be used for different segmentations. Therefore, different passes of the multi-pass inspection may detect different types of defects. In this manner, the results of the different passes of the multi-pass inspection can be combined to generate the overall inspection results for the wafer. The results of the defects detected using the raw output acquired in different passes may be combined after defect detection using the raw output generated in all of the different passes has been performed. Alternatively, the defect detection results generated using the raw output acquired in different passes may be combined on-the-fly or while some of the raw output is still being acquired.

In an additional embodiment, the method includes applying one or more predetermined defect detection parameters to the first or second raw output to detect additional defects on the wafer and combining the defects and the additional defects to generate inspection results for the wafer. For example, a reference (such as an 8-bit reference image) may be subtracted from the individual output in the first or second raw output (such as an 8-bit test image) regardless of the segment to which the individual output in the first or second raw output has been assigned. The reference may include any suitable reference such as those described above. In addition, the same reference can be used for detecting defects by applying the assigned one or more defect detection parameters to the individual output in the second raw output and by applying one or more predetermined defect detection parameters to the first or second raw output. The result of the subtraction may be an absolute difference. A predetermined, direct difference threshold may then be applied to the absolute difference, and any individual output having an absolute difference above the threshold may be identified as a defect. In addition, the same predetermined, direct difference threshold may be applied to the absolute difference regardless of the segment to which the individual output in the second raw output has been assigned. Defects detected in this manner may then be combined with defects detected by applying the assigned one or more defect detection parameters to the individual output in the second raw output to generate the final inspection results for the wafer. For example, a defective mask may be separately generated for all defects detected in any manner. Region "grow" may be performed from both difference images, and a final mask for all defects may be generated.

Detecting defects in different manners as described above may provide defect redetection, which may be advantageous for a number of reasons. For example, automatic 2D projection and geometry-based segmentation provide robust defect redetection and ease of use for defect redetection. In addition, the segmentation described herein provides a dynamic way of mapping defect and reference images. For example, if the segment is noisy, the difference can be detuned. In contrast, if the segment is cleaner, the difference can be enlarged. In addition, double detection as described above lowers the possibility of false alarms from either detection method.

The method may also include storing results of any of the step(s) of the method in a storage medium. The results may include any of the results described herein and may be stored in any manner known in the art. For example, the segments to which the individual output is assigned and/or the one or more defect detection parameters assigned to the different segments may be used to generate a data structure such as a look up table that is stored on a storage medium coupled to the inspection system. The storage medium may include any suitable storage medium known in the art. After the results have been stored, the results can be accessed in the storage medium and used as described herein, formatted for display to a user, used by another software module, method, or system, etc. Storing the results may also be performed as described in commonly owned U.S. Patent Application Publication No. 2009/0080759 by Bhaskar et al. published on Mar. 26, 2009, which is incorporated by reference as if fully set forth herein.

Figure 3:
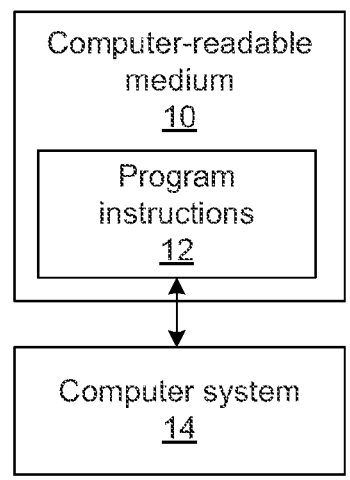
FIG. 3 is a block diagram illustrating one embodiment of a non-transitory computer-readable medium that includes program instructions executable on a computer system for performing one or more of the method embodiments described herein.

Another embodiment relates to a non-transitory computer-readable medium storing program instructions executable on a computer system for performing a method (i.e., a computer-implemented method) for detecting defects on a wafer. One such embodiment is shown in FIG. 3. For example, as shown in FIG. 3, non-transitory computer-readable medium 10 includes program instructions 12 executable on computer system 14 for performing the method for detecting defects on a wafer described above. The computer-implemented method for which the program instructions are executable may include any other step(s) of any other method(s) described herein.

Program instructions 12 implementing methods such as those described herein may be stored on non-transitory computer-readable medium 10. The computer-readable medium may be a storage medium such as a magnetic or optical disk, a magnetic tape or any other suitable computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 14 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Figure 4:
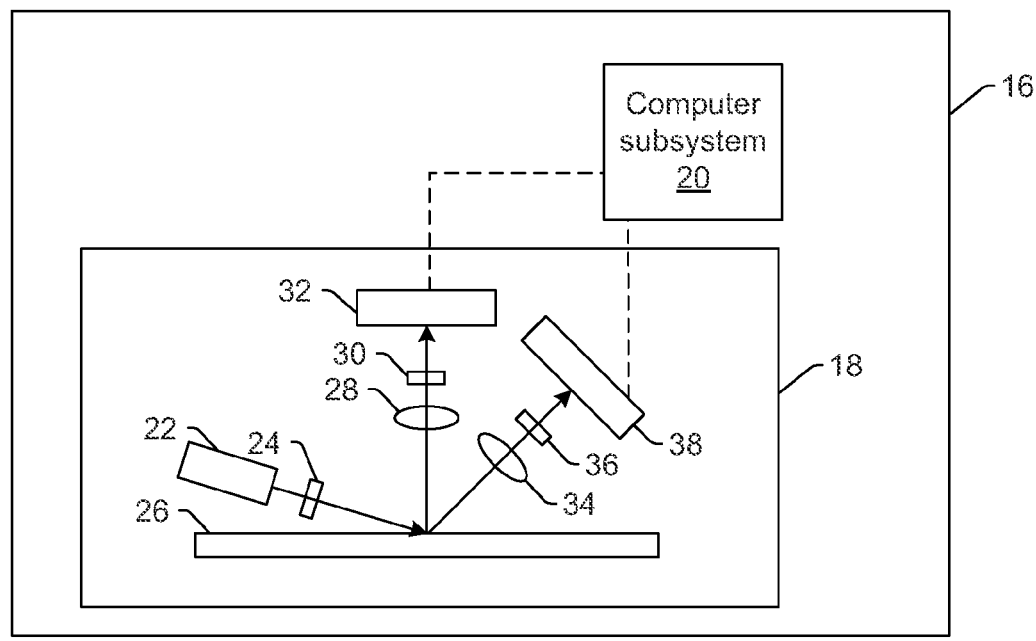
FIG. 4 is a schematic diagram illustrating a side view of one embodiment of a system configured to detect defects on a wafer.

An additional embodiment relates to a system configured to detect defects on a wafer. One embodiment of such a system is shown in FIG. 4. As shown in FIG. 4, system 16 includes inspection subsystem 18 and computer subsystem 20. The inspection subsystem is configured to generate first raw output for a wafer by scanning the wafer using a first optics mode of the inspection subsystem and to generate second raw output for the wafer by scanning the wafer using a second optics mode of the inspection subsystem. For example, as shown in FIG. 4, the inspection subsystem includes light source 22 such as a laser. Light source 22 is configured to direct light to polarizing component 24. In addition, the inspection subsystem may include more than one polarizing component (not shown), each of which may be positioned independently in the path of the light from the light source. Each of the polarizing components may be configured to alter the polarization of the light from the light source in a different manner. The inspection subsystem may be configured to move the polarizing components into and out of the path of the light from the light source in any suitable manner depending on which polarization setting is selected for illumination of the wafer during a scan. The polarization setting used for the illumination of the wafer during a scan may include p-polarized (P), s-polarized (S), or circularly polarized (C).

Light exiting polarizing component 24 is directed to wafer 26 at an oblique angle of incidence, which may include any suitable oblique angle of incidence. The inspection subsystem may also include one or more optical components (not shown) that are configured to direct light from light source 22 to polarizing component 24 or from polarizing component 24 to wafer 26. The optical components may include any suitable optical components known in the art such as, but not limited to, a reflective optical component. In addition, the light source, the polarizing component, and/or the one or more optical components may be configured to direct the light to the wafer at one or more angles of incidence (e.g., an oblique angle of incidence and/or a substantially normal angle of incidence). The inspection subsystem may be configured to perform the scanning by scanning the light over the wafer in any suitable manner.

Light scattered from wafer 26 may be collected and detected by multiple channels of the inspection subsystem during scanning. For example, light scattered from wafer 26 at angles relatively close to normal may be collected by lens 28. Lens 28 may include a refractive optical element as shown in FIG. 4. In addition, lens 28 may include one or more refractive optical elements and/or one or more reflective optical elements. Light collected by lens 28 may be directed to polarizing component 30, which may include any suitable polarizing component known in the art. In addition, the inspection subsystem may include more than one polarizing component (not shown), each of which may be positioned independently in the path of the light collected by the lens. Each of the polarizing components may be configured to alter the polarization of the light collected by the lens in a different manner. The inspection subsystem may be configured to move the polarizing components into and out of the path of the light collected by the lens in any suitable manner depending on which polarization setting is selected for detection of the light collected by lens 28 during scanning. The polarization setting used for the detection of the light collected by lens 28 during scanning may include any of the polarization settings described herein (e.g., P, S, and unpolarized (N)).

Light exiting polarizing component 30 is directed to detector 32. Detector 32 may include any suitable detector known in the art such as a charge coupled device (CCD) or another type of imaging detector. Detector 32 is configured to generate raw output that is responsive to the scattered light collected by lens 28 and transmitted by polarizing component 30 if positioned in the path of the collected scattered light. Therefore, lens 28, polarizing component 30 if positioned in the path of the light collected by lens 28, and detector 32 form one channel of the inspection subsystem. This channel of the inspection subsystem may include any other suitable optical components (not shown) known in the art such as a Fourier filtering component.

Light scattered from wafer 26 at different angles may be collected by lens 34. Lens 34 may be configured as described above. Light collected by lens 34 may be directed to polarizing component 36, which may include any suitable polarizing component known in the art. In addition, the inspection subsystem may include more than one polarizing component (not shown), each of which may be positioned independently in the path of the light collected by the lens. Each of the polarizing components may be configured to alter the polarization of the light collected by the lens in a different manner. The inspection subsystem may be configured to move the polarizing components into and out of the path of the light collected by the lens in any suitable manner depending on which polarization setting is selected for detection of the light collected by lens 34 during scanning. The polarization setting used for detection of the light collected by lens 34 during scanning may include P, S, or N.

Light exiting polarizing component 36 is directed to detector 38, which may be configured as described above. Detector 38 is also configured to generate raw output that is responsive to the collected scattered light that passes through polarizing component 36 if positioned in the path of the scattered light. Therefore, lens 34, polarizing component 36 if positioned in the path of the light collected by lens 34, and detector 38 may form another channel of the inspection subsystem. This channel may also include any other optical components (not shown) described above. In some embodiments, lens 34 may be configured to collect light scattered from the wafer at polar angles from about 20 degrees to about 70 degrees. In addition, lens 34 may be configured as a reflective optical component (not shown) that is configured to collect light scattered from the wafer at azimuthal angles of about 360 degrees.

The inspection subsystem shown in FIG. 4 may also include one or more other channels (not shown). For example, the inspection subsystem may include an additional channel, which may include any of the optical components described herein such as a lens, one or more polarizing components, and a detector, configured as a side channel. The lens, the one or more polarizing components, and the detector may be further configured as described herein. In one such example, the side channel may be configured to collect and detect light that is scattered out of the plane of incidence (e.g., the side channel may include a lens, which is centered in a plane that is substantially perpendicular to the plane of incidence, and a detector configured to detect light collected by the lens).

When generating raw output using multiple optics modes having one or more different values for one or more optical parameters of the inspection system, the values of any optical parameter(s) of the inspection subsystem may be altered in any suitable manner if necessary. For example, to change the illumination polarization states for different optics modes, polarizing component 24 may be removed and/or replaced as described herein with a different polarizing component. In another example, to change illumination angles for different optics modes, the position of the light source and/or any other optical components (e.g., polarizing component 24) used to direct the light to the wafer may be altered in any suitable manner.

Computer subsystem 20 is configured to acquire the first and second raw output generated by the inspection subsystem. For example, first and second raw output generated by the detector(s) during scanning may be provided to computer subsystem 20. In particular, the computer subsystem may be coupled to each of the detectors (e.g., by one or more transmission media shown by the dashed lines in FIG. 4, which may include any suitable transmission media known in the art) such that the computer subsystem may receive the first and second raw output generated by the detector(s). The computer subsystem may be coupled to each of the detectors in any suitable manner. The first and second raw output generated by the detector(s) during scanning of the wafer may include any of the first and second raw output described herein.

The computer subsystem is configured to identify one or more characteristics of the first raw output that correspond to one or more geometrical characteristics of patterned features formed on the wafer according to any of the embodiments described herein. The one or more characteristics of the first raw output may include any such characteristics described herein. The one or more geometrical characteristics may also include any such characteristics described herein. The patterned features may include any of the patterned features described herein.

In addition, the computer subsystem is configured to assign individual output in the second raw output to different segments based on the identified one or more characteristics of the first raw output and based on the individual output in the second raw output and individual output in the first raw output that were generated at substantially the same locations on the wafer such that the one or more geometrical characteristics of the patterned features that correspond to each of the different segments in the second raw output are different. The computer subsystem may be configured to assign the individual output of the second raw output to the different segments according to any of the embodiments described herein. The individual output may include any of the individual output described herein. The different segments may be configured as described herein. The identified one or more characteristics of the first raw output may include any such characteristics described herein.

The computer subsystem is further configured to separately assign one or more defect detection parameters to the different segments according to any of the embodiments described herein. The one or more defect detection parameters may include any of the defect detection parameters described herein. The computer subsystem is also configured to apply the assigned one or more defect detection parameters to the individual output in the second raw output assigned to the different segments to thereby detect defects on the wafer, which may be performed according to any of the embodiments described herein. The assigned one or more defect detection parameters may include any such parameters described herein.

The computer subsystem may be configured to perform any other step(s) of any method embodiment(s) described herein. The computer subsystem, the inspection subsystem, and the system may be further configured as described herein.

It is noted that FIG. 4 is provided herein to generally illustrate one configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection system) such as the Puma 90xx, 91xx, and 93xx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

The embodiments described herein may also be implemented on a variety of multi-channel or multi-perspective inspection systems. For example, one multi-perspective inspection system may be a deep ultraviolet (DUV) system that includes two collectors optimized for defect detection in addition to a top relatively large numerical aperture (NA) collector and uses flood illumination with imaging optics. In such a system, the embodiments described herein may use raw output generated by the top collector, which is the largest and has the highest resolution, for segment definition and its side collectors can use the segment information to improve defect detection sensitivity.

Further modifications and alternative embodiments of various aspects of the invention will be apparent to those skilled in the art in view of this description. For example, methods and systems for detecting defects on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects on a wafer, comprising:
    acquiring first raw output for a wafer generated using a first optics mode of an inspection system and second raw output generated for the wafer using a second optics mode of the inspection system;
    identifying one or more characteristics of the first raw output that correspond to one or more geometrical characteristics of patterned features formed on the wafer;
    assigning individual output in the second raw output to different segments based on the identified one or more characteristics of the first raw output and based on the individual output in the second raw output and individual output in the first raw output that were generated at substantially the same locations on the wafer such that the one or more geometrical characteristics of the patterned features that correspond to each of the different segments in the second raw output are different, wherein the one or more geometrical characteristics that correspond to one of the different segments comprise one or more geometrical characteristics of page breaks, and wherein the one or more geometrical characteristics that correspond to another of the different segments comprise one or more geometrical characteristics of array areas;
    separately assigning one or more defect detection parameters to the different segments; and
    applying the assigned one or more defect detection parameters to the individual output in the second raw output assigned to the different segments to thereby detect defects on the wafer.

2. The method of claim 1, wherein the first and second optics modes are defined by different detectors of the inspection system and the same values for other optical parameters of the inspection system.

3. The method of claim 1, wherein first and second optics modes are defined by different detectors of the inspection system, one or more different values for one or more optical parameters of the inspection system, and the same values for other optical parameters of the inspection system.

4. The method of claim 1, wherein the first and second optics modes are defined by the same detector of the inspection system, one or more different values for one or more optical parameters of the inspection system, and the same values for other optical parameters of the inspection system.

5. The method of claim 1, wherein the first and second optics modes are defined as a combination of the same set of detectors of the inspection system, one or more different values for one or more optical parameters of the inspection system, and the same values for other optical parameters of the inspection system.

6. The method of claim 1, wherein the first and second optics modes are defined as a combination of a subset of detectors of the inspection system, one or more different values for one or more optical parameters of the inspection system, and the same values for other optical parameters of the inspection system.

7. The method of claim 1, wherein the first and second raw output is responsive to light scattered from the wafer.

8. The method of claim 1, wherein the first and second raw output is responsive to light reflected from the wafer.

9. The method of claim 1, wherein the identified one or more characteristics of the first raw output comprise projections along lines within the first raw output.

10. The method of claim 1, wherein the identified one or more characteristics of the first raw output comprise median intensity of the first raw output that corresponds to the one or more geometrical characteristics of the patterned features.

11. The method of claim 1, wherein the one or more geometrical characteristics of the patterned features further comprise edges, shape, texture, a mathematical calculation that defines geometry of the patterned features, or some combination thereof.

12. The method of claim 1, wherein said identifying is performed based on how a design layout of the patterned features will affect the one or more characteristics of the first raw output.

13. The method of claim 1, wherein said identifying is performed while said acquiring is being performed.

14. The method of claim 1, wherein said identifying and said assigning the individual output are performed automatically without user input.

15. The method of claim 1, wherein said assigning the individual output is performed without regard to design data associated with the patterned features.

16. The method of claim 1, wherein said assigning the individual output is performed without regard to intensity of the individual output in the second raw output.

17. The method of claim 1, wherein said assigning the individual output comprises analyzing the identified one or more characteristics of the first raw output and applying thresholds to the individual output of the second raw output.

18. The method of claim 1, wherein the one or more characteristics of the first raw output that correspond to the one or more geometrical characteristics of some of the patterned features cannot be suppressed by filtering.

19. The method of claim 1, wherein the one or more defect detection parameters comprise a threshold to be applied to a difference between the individual output in the second raw output and a reference.

20. The method of claim 1, wherein said separately assigning the one or more defect detection parameters is performed such that defects are detected using the individual output of the second raw output assigned to the different segments with different sensitivities.

21. The method of claim 1, wherein said acquiring is performed in one pass of a multi-pass inspection of the wafer, and wherein the computer-implemented method is not performed for raw output acquired in another pass of the multi-pass inspection.

22. The method of claim 1, wherein said acquiring is performed in one pass of a multi-pass inspection of the wafer, and wherein the computer-implemented method is performed for raw output acquired in another pass of the multi-pass inspection.

23. The method of claim 1, wherein said acquiring is performed in one pass of a multi-pass inspection of the wafer, wherein the computer-implemented method is not performed for raw output acquired in another pass of the multi-pass inspection, wherein additional defects are detected using the raw output acquired in the other pass, and wherein the method further comprises combining the defects and the additional defects to generate inspection results for the wafer.

24. The method of claim 1, wherein said acquiring is performed in one pass of a multi-pass inspection of the wafer, wherein the computer-implemented method is performed for raw output acquired in another pass of the multi-pass inspection, wherein additional defects are detected using the raw output acquired in the other pass, and wherein the method further comprises combining the defects and the additional defects to generate inspection results for the wafer.

25. The method of claim 1, further comprising applying one or more predetermined defect detection parameters to the first or second raw output to detect additional defects on the wafer and combining the defects and the additional defects to generate inspection results for the wafer.

26. A non-transitory computer-readable medium, storing program instructions executable on a computer system for performing a method for detecting defects on a wafer, wherein the method comprises:

acquiring first raw output for a wafer generated using a first optics mode of an inspection system and second raw output generated for the wafer using a second optics mode of the inspection system;

identifying one or more characteristics of the first raw output that correspond to one or more geometrical characteristics of patterned features formed on the wafer;

assigning individual output in the second raw output to different segments based on the identified one or more characteristics of the first raw output and based on the individual output in the second raw output and individual output in the first raw output that were generated at substantially the same locations on the wafer such that the one or more geometrical characteristics of the patterned features that correspond to each of the different segments in the second raw output are different, wherein the one or more geometrical characteristics that correspond to one of the different segments comprise one or more geometrical characteristics of page breaks, and wherein the one or more geometrical characteristics that correspond to another of the different segments comprise one or more geometrical characteristics of array area;

separately assigning one or more defect detection parameters to the different segments; and applying the assigned one or more defect detection parameters to the individual output in the second raw output assigned to the different segments to thereby detect defects on the wafer.

27. A system configured to detect defects on a wafer, comprising:

an inspection subsystem configured to generate first raw output for a wafer by scanning the wafer using a first optics mode of the inspection subsystem and to generate second raw output for the wafer by scanning the wafer using a second optics mode of the inspection subsystem; and a computer subsystem configured to:

acquire the first and second raw output;

identify one or more characteristics of the first raw output that correspond to one or more geometrical characteristics of patterned features formed on the wafer;

assign individual output in the second raw output to different segments based on the identified one or more characteristics of the first raw output and based on the individual output in the second raw output and individual output in the first raw output that were generated at substantially the same locations on the wafer such that the one or more geometrical characteristics of the patterned features that correspond to each of the different segments in the second raw output are different, wherein the one or more geometrical characteristics that correspond to one of the different segments comprise one or more geometrical characteristics of page breaks, and wherein the one or more geometrical characteristics that correspond to another of the different segments comprise one or more geometrical characteristics of array areas;

separately assign one or more defect detection parameters to the different segments; and apply the assigned one or more defect detection parameters to the individual output in the second raw output assigned to the different segments to thereby detect defects on the wafer.

28. The system of claim 27, wherein the first and second optics modes are defined by different detectors of the inspection subsystem and the same values for other optical parameters of the inspection subsystem.

29. The system of claim 27, wherein first and second optics modes are defined by different detectors of the inspection subsystem, one or more different values for one or more optical parameters of the inspection subsystem, and the same values for other optical parameters of the inspection subsystem.

30. The system of claim 27, wherein the first and second optics modes are defined by the same detector of the inspection subsystem, one or more different values for one or more optical parameters of the inspection subsystem, and the same values for other optical parameters of the inspection subsystem.

31. The system of claim 27, wherein the first and second optics modes are defined as a combination of the same set of detectors of the inspection subsystem, one or more different values for one or more optical parameters of the inspection subsystem, and the same values for other optical parameters of the inspection subsystem.

32. The system of claim 27, wherein the first and second optics modes are defined as a combination of a subset of detectors of the inspection subsystem, one or more different values for one or more optical parameters of the inspection subsystem, and the same values for other optical parameters of the inspection subsystem.

33. The system of claim 27, wherein the first and second raw output is responsive to light scattered from the wafer.

34. The system of claim 27, wherein the first and second raw output is responsive to light reflected from the wafer.

35. The system of claim 27, wherein the identified one or more characteristics of the first raw output comprise projections along lines within the first raw output.

36. The system of claim 27, wherein the identified one or more characteristics of the first raw output comprise median intensity of the first raw output that corresponds to the one or more geometrical characteristics of the patterned features.

37. The system of claim 27, wherein the one or more geometrical characteristics of the patterned features further comprise edges, shape, texture, a mathematical calculation that defines geometry of the patterned features, or some combination thereof.

38. The system of claim 27, wherein the computer subsystem is further configured to identify the one or more characteristics based on how a design layout of the patterned features will affect the one or more characteristics of the first raw output.

39. The system of claim 28, wherein the computer subsystem is further configured to identify the one or more characteristics while the computer subsystem acquires the first and second raw output.

40. The system of claim 27, wherein the computer subsystem is further configured to identify the one or more characteristics and assign the individual output in the second raw output to the different segments automatically without user input.

41. The system of claim 27, wherein the computer subsystem is further configured to assign the individual output in the second raw output to the different segments without regard to design data associated with the patterned features.

42. The system of claim 27, wherein the computer subsystem is further configured to assign the individual output in the second raw output to the different segments without regard to intensity of the individual output in the second raw output.

43. The system of claim 27, wherein the computer subsystem is further configured to assign the individual output in the second raw output to the different segments by analyzing the identified one or more characteristics of the first raw output and applying thresholds to the individual output of the second raw output.

44. The system of claim 27, wherein the one or more characteristics of the first raw output that correspond to the one or more geometrical characteristics of some of the patterned features cannot be suppressed by filtering.

45. The system of claim 27, wherein the one or more defect detection parameters comprise a threshold to be applied to a difference between the individual output in the second raw output and a reference.

46. The system of claim 27, wherein the computer subsystem is further configured to separately assign the one or more defect detection parameters such that defects are detected using the individual output of the second raw output assigned to the different segments with different sensitivities.

47. The system of claim 27, wherein the inspection subsystem is further configured to generate the first and second raw output in one pass of a multi-pass inspection of the wafer, and wherein the computer subsystem is not configured to identify the one or more characteristics, assign the individual output, separately assign the one or more defect detection parameters, or apply the assigned one or more defect detection parameters for raw output acquired in another pass of the multi-pass inspection.

48. The system of claim 27, wherein the inspection subsystem is further configured to generate the first and second raw output in one pass of a multi-pass inspection of the wafer, and wherein the computer subsystem is further configured to identify the one or more characteristics, assign the individual output, separately assign the one or more defect detection parameters, and apply the assigned one or more defect detection parameters for raw output acquired in another pass of the multi-pass inspection.

49. The system of claim 27, wherein the inspection subsystem is further configured to generate the first and second raw output in one pass of a multi-pass inspection of the wafer, wherein the computer subsystem is not configured to identify the one or more characteristics, assign the individual output, separately assign the one or more defect detection parameters, or apply the assigned one or more defect detection parameters for raw output acquired in another pass of the multi-pass inspection, wherein additional defects are detected using the raw output acquired in the other pass, and wherein the computer subsystem is further configured to combine the defects and the additional defects to generate inspection results for the wafer.

50. The system of claim 27, wherein the inspection subsystem is further configured to generate the first and second raw output in one pass of a multi-pass inspection of the wafer, wherein the computer subsystem is further configured to identify the one or more characteristics, assign the individual output, separately assign the one or more defect detection parameters, and apply the assigned one or more defect detection parameters for raw output acquired in another pass of the multi-pass inspection, wherein additional defects are detected using the raw output acquired in the other pass, and wherein the computer subsystem is further configured to combine the defects and the additional defects to generate inspection results for the wafer.

51. The system of claim 27, wherein the computer subsystem is further configured to apply one or more predetermined defect detection parameters to the first or second raw output to detect additional defects on the wafer and combine the defects and the additional defects to generate inspection results for the wafer.

* * * * *